US009481913B2

(12) United States Patent
Burns

(10) Patent No.: US 9,481,913 B2
(45) Date of Patent: Nov. 1, 2016

(54) SEQUENCES AND THEIR USE FOR DETECTION AND CHARACTERIZATION OF E. COLI O157:H7

(71) Applicant: E.I. du Pont de Nemours and Company, Wilmington, DE (US)

(72) Inventor: Frank R. Burns, Philadelphia, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 186 days.

(21) Appl. No.: 14/475,035

(22) Filed: Sep. 2, 2014

(65) Prior Publication Data

US 2014/0371104 A1 Dec. 18, 2014

Related U.S. Application Data

(62) Division of application No. 12/839,837, filed on Jul. 20, 2010, now Pat. No. 8,846,349.

(60) Provisional application No. 61/227,622, filed on Jul. 22, 2009.

(51) Int. Cl.
C12Q 1/68 (2006.01)
C12P 19/34 (2006.01)

(52) U.S. Cl.
CPC ........... *C12Q 1/689* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,654,417 A | 8/1997 | Tarr et al. | |
| 6,326,145 B1 | 12/2001 | Whitcombe et al. | |
| 6,365,723 B1 | 4/2002 | Blattner et al. | |
| 6,855,814 B2 | 2/2005 | Blattner et al. | |
| 7,125,661 B1 | 10/2006 | Reeves et al. | |
| 7,148,005 B2 | 12/2006 | Reeves et al. | |
| 8,846,349 B2 * | 9/2014 | Burns | C12Q 1/689 435/6.1 |
| 2003/0023075 A1 | 1/2003 | Blattner et al. | |
| 2006/0094034 A1 | 5/2006 | Brousseau et al. | |
| 2008/0057034 A1 | 3/2008 | Hassan et al. | |
| 2008/0113342 A1 | 5/2008 | Cao et al. | |
| 2008/0184386 A1 | 7/2008 | Cao et al. | |

FOREIGN PATENT DOCUMENTS

| | | |
|---|---|---|
| CN | 1680602 A | 10/2005 |
| CN | 1749414 A | 3/2006 |
| CN | 101113475 A | 1/2008 |
| CN | 101113476 A | 1/2008 |
| CN | 101153331 A | 4/2008 |
| EP | 1239041 A2 | 9/2002 |
| EP | 1770171 A1 | 4/2007 |
| EP | 1944377 A2 | 7/2008 |
| JP | 2002355074 A | 12/2002 |
| WO | WO 96/32405 A1 | 10/1996 |
| WO | WO 98/50531 A1 | 11/1998 |
| WO | WO 99/04039 A1 | 1/1999 |
| WO | WO 99/61458 A1 | 12/1999 |
| WO | WO 02/052035 A2 | 7/2002 |
| WO | WO 03/062464 A2 | 7/2003 |
| WO | WO 2005/087930 A1 | 9/2005 |
| WO | WO 2005/090596 A2 | 9/2005 |
| WO | WO 2006/012323 A1 | 2/2006 |
| WO | WO 2006/057341 A1 | 6/2006 |
| WO | WO 2006/069198 A1 | 6/2006 |
| WO | WO 2007/024756 A2 | 3/2007 |
| WO | WO 2007/118162 A1 | 10/2007 |
| WO | WO 2008/027560 A2 | 3/2008 |

OTHER PUBLICATIONS

Buck, et al., (Biotechniques, 1999, 27(3); pp. 528-536).
Ibekwe, A., et al., "Multiplex Flurogenic Real-Time PCR for Detection and Quantification . . . " Applied and Environmental Microbiology, vol. 68, p. 4853-4862 (Oct. 2002).
International Search Report and Written Opinion of the International Searching Authority, Application No. PCT/US2010/042570, Mailed Oct. 20, 2010.
Klerks, M., et al., "Comparison of real-time PCR methods for detection of Salmonella . . . " J. of Microbiological Methods, vol. 59, p. 337-349 (2004).
Lowe, et al., (Nucleic Acids Research, vol. 18, No. 7, pp. 1757-1761, 1990).
Makino, K., et al., "Complete nucleotide sequence of 93-kb and 3.3-kb plasmids of an enterohemorrhagic *Escherichia coli* . . ." DNA Res., vol. 5, p. 1-9 (1998).
Mull, B., et al., "Recovery and Detection of *Escherichia coli* O157:H7 in Surface Water Using . . . " Applied and Environmental Microbiology, vol. 75, p. 3593-3597 (Jun. 2009).
NCBI Genbank Accession No. AR204116 (Jun. 20, 2002).
NCBI Genbank Accession No. AF163335 (Dec. 28, 2000).
NCBI Genbank Accession No. AF061251 (Aug. 20, 1998).
Perna, N., et al., "Genome sequence of enterohaemorrhagic *Escherichia coli* O157:H7", Nature, vol. 409, p. 529-533 (Jan. 25, 2001).
Perelle, S., et al., "Detection by 5'-nuclease PCR of Shiga-toxin producing *Escherichia coli* . . . " Molec. and Cell. Probes, vol. 18, p. 185-192 (2004).
Sharma, V.K. et al, "Semi-automated fluorogenic PCR assays (Taq-Man) for rapid detection of *Escherichia* . . . " Molecular and Cellular Probes 13, p. 291-302 (1999).

(Continued)

Primary Examiner — Young J Kim

(57) ABSTRACT

This invention relates to a rapid method for detection and characterization of *Escherichia coli* bacteria serotype O157:H7 based on the presence of nucleic acid sequences, in particular, to a PCR-based method for detection, and to oligonucleotide molecules and reagents and kits useful therefore. This method is preferably employed to detect *E. coli* O157:H7 in a food or water sample, such as a beef enrichment. The present invention further relates to replication compositions and kits for carrying out the method of the present invention.

4 Claims, No Drawings

(56) References Cited

OTHER PUBLICATIONS

Sharma, V.K., et al., "Real-time reverse transcription-multiplex PCR for simultaneous . . . " Molecular and Cellular Probes 20, p. 298-306 (Oct. 1, 2006).

Singh, J., et al., "A Scorpion Probe-Based Real-Time PCR Assay . . . ", Foodborne Pathogens and Disease, vol. 6, No. 3, p. 395-400 (Apr. 2009).

Wang, L, et al., "Orginazation of *Escherichia coli* O157 O Antigen Gene . . . " Infection and Immunity, vol. 66, No. 8, p. 3545-3551 (Aug. 1998).

Wick, Lucus, et al.; Evolution of Genomic Content in the Stepwise Emergence of *Escherichia coli* O157:H7+; J. of Bacteriology, Mar. 2005, p. 1783-1791.

Database Geneseq [Online], "*Escherichia coli* detecting probe sequence, SEQ ID 331.", retrieved from EBI accession No. AW049752 (Jun. 11, 2009).

Thelwell, et al., "Mode of action and application of Scorpion primers to mutation detection", Nucleic Acids Research, 2000, vol. 28, No. 19, pp. 3752-3761.

Office Action for corresponding Canadian Application No. 2,768,794, dated Apr. 7, 2016.

* cited by examiner

SEQUENCE LISTING

<160> NUMBER OF SEQ ID NOS: 29

<210> SEQ ID NO 1
<211> LENGTH: 181
<212> TYPE: DNA
<213> ORGANISM: Escherichia coli

<400> SEQUENCE: 1

```
ggcactgaat ttattaagag attgcaaaga cattaagggt ggggtgaaga ggaaaagaaa      60
gaaggttgcg ttaaacacat gttatataga agaagtgctt gcatcctgct cagagcttgg    120
gtttcgaact gacaaaatga aaaatttaac acagatttaa ttcatgctct tgccctgcgg    180
g                                                                    181
```

<210> SEQ ID NO 2
<211> LENGTH: 168
<212> TYPE: DNA
<213> ORGANISM: Escherichia coli

<400> SEQUENCE: 2

```
ctacaggtga aggtggaatg gttgtcacga atgacaaaac actttatgac cgttgtttac      60
attttaaagg ccaaggatta gctgtacata ggcaatattg gcatgacgtt ataggctaca    120
attataggac gacaaatatc tgcgctgcta taggattagc ccagttag                  168
```

<210> SEQ ID NO 3
<211> LENGTH: 218
<212> TYPE: DNA
<213> ORGANISM: Escherichia coli

<400> SEQUENCE: 3

```
atccagcaag agaaatgaaa agatcgccaa catctatttta atgggaatgc gaaaacacgt     60
tccaaatggg actaatgttt aaaatatata taatttcgct aatttactaa attatggctt    120
cttttttaagc tatcctttac ttagttatta ctgatacagc atgaaattta taatactctg    180
atacattttt atacgttatt caagccgcat atctagcg                             218
```

<210> SEQ ID NO 4
<211> LENGTH: 86
<212> TYPE: DNA
<213> ORGANISM: Artificial Sequence
<220> FEATURE:
<223> OTHER INFORMATION: Primer-probe complex

<400> SEQUENCE: 4

```
aacccaccca cgcaaccttc tttcttttcc tcttcacggg tgggttggca ctgaatttat      60
taagagattg caaagacatt aagggt                                           86
```

<210> SEQ ID NO 5
<211> LENGTH: 32

```
<212> TYPE: DNA
<213> ORGANISM: Artificial Sequence
<220> FEATURE:
<223> OTHER INFORMATION: Primer/probe

<400> SEQUENCE: 5
cccgcagggc aagagcatga attaaatctg tg                                32

<210> SEQ ID NO 6
<211> LENGTH: 40
<212> TYPE: DNA
<213> ORGANISM: Artificial Sequence
<220> FEATURE:
<223> OTHER INFORMATION: Primer/probe

<400> SEQUENCE: 6
ggcactgaat ttattaagag attgcaaaga cattaagggt                        40

<210> SEQ ID NO 7
<211> LENGTH: 28
<212> TYPE: DNA
<213> ORGANISM: Artificial Sequence
<220> FEATURE:
<223> OTHER INFORMATION: Primer/probe

<400> SEQUENCE: 7
acgcaacctt ctttcttttc ctcttcac                                     28

<210> SEQ ID NO 8
<211> LENGTH: 15
<212> TYPE: DNA
<213> ORGANISM: Artificial Sequence
<220> FEATURE:
<223> OTHER INFORMATION: Primer/probe

<400> SEQUENCE: 8
tgaattaaat ctgtg                                                   15

<210> SEQ ID NO 9
<211> LENGTH: 15
<212> TYPE: DNA
<213> ORGANISM: Artificial Sequence
<220> FEATURE:
<223> OTHER INFORMATION: Primer/probe

<400> SEQUENCE: 9
aaaatttaac acaga                                                   15

<210> SEQ ID NO 10
<211> LENGTH: 66
<212> TYPE: DNA
<213> ORGANISM: Artificial Sequence
<220> FEATURE:
<223> OTHER INFORMATION: Primer-probe complex

<400> SEQUENCE: 10
tttaaaatgt aaacaacggt cataaagtgt tttgctacag gtgaaggtgg aatggttgtc  60
acgaat                                                             66

<210> SEQ ID NO 11
<211> LENGTH: 34
<212> TYPE: DNA
<213> ORGANISM: Artificial Sequence
<220> FEATURE:
<223> OTHER INFORMATION: Blocking oligonucleotide
```

```
<400> SEQUENCE: 11
caaaacactt tatgaccgtt gtttacattt taaa                              34

<210> SEQ ID NO 12
<211> LENGTH: 32
<212> TYPE: DNA
<213> ORGANISM: Artificial Sequence
<220> FEATURE:
<223> OTHER INFORMATION: Primer/probe

<400> SEQUENCE: 12
ctaactgggc taatcctata gcagcgcaga ta                                32

<210> SEQ ID NO 13
<211> LENGTH: 32
<212> TYPE: DNA
<213> ORGANISM: Artificial Sequence
<220> FEATURE:
<223> OTHER INFORMATION: Primer/probe

<400> SEQUENCE: 13
ctacaggtga aggtggaatg gttgtcacga at                                32

<210> SEQ ID NO 14
<211> LENGTH: 29
<212> TYPE: DNA
<213> ORGANISM: Artificial Sequence
<220> FEATURE:
<223> OTHER INFORMATION: Primer/probe

<400> SEQUENCE: 14
acattttaaa ggccaaggat tagctgtac                                    29

<210> SEQ ID NO 15
<211> LENGTH: 87
<212> TYPE: DNA
<213> ORGANISM: Artificial Sequence
<220> FEATURE:
<223> OTHER INFORMATION: Primer-probe complex

<400> SEQUENCE: 15
aacccacccc ccatttggaa cgtgttttcg cattccgggt gggttatcca gcaagagaaa  60
tgaaaagatc gccaacatct atttaat                                      87

<210> SEQ ID NO 16
<211> LENGTH: 41
<212> TYPE: DNA
<213> ORGANISM: Artificial Sequence
<220> FEATURE:
<223> OTHER INFORMATION: Primer/probe

<400> SEQUENCE: 16
cgctagatat gcggcttgaa taacgtataa aaatgtatca g                      41

<210> SEQ ID NO 17
<211> LENGTH: 42
<212> TYPE: DNA
<213> ORGANISM: Artificial Sequence
<220> FEATURE:
<223> OTHER INFORMATION: Primer/probe

<400> SEQUENCE: 17
atccagcaag agaaatgaaa agatcgccaa catctattta at                     42
```

```
<210> SEQ ID NO 18
<211> LENGTH: 33
<212> TYPE: DNA
<213> ORGANISM: Artificial Sequence
<220> FEATURE:
<223> OTHER INFORMATION: Primer/probe

<400> SEQUENCE: 18
tatggcttct ttttaagcta tcctttactt agt                                    33

<210> SEQ ID NO 19
<211> LENGTH: 15
<212> TYPE: DNA
<213> ORGANISM: Artificial Sequence
<220> FEATURE:
<223> OTHER INFORMATION: Primer/probe

<400> SEQUENCE: 19
caacatctat ttaat                                                         15

<210> SEQ ID NO 20
<211> LENGTH: 15
<212> TYPE: DNA
<213> ORGANISM: Artificial Sequence
<220> FEATURE:
<223> OTHER INFORMATION: Primer/probe

<400> SEQUENCE: 20
gttttcgcat tccca                                                         15

<210> SEQ ID NO 21
<211> LENGTH: 26
<212> TYPE: DNA
<213> ORGANISM: Artificial Sequence
<220> FEATURE:
<223> OTHER INFORMATION: Primer/probe

<400> SEQUENCE: 21
aatagcagac actctatgcc tgtgtg                                             26

<210> SEQ ID NO 22
<211> LENGTH: 26
<212> TYPE: DNA
<213> ORGANISM: Artificial Sequence
<220> FEATURE:
<223> OTHER INFORMATION: Primer/probe

<400> SEQUENCE: 22
tatttacacc acaaaggaaa aagctg                                             26

<210> SEQ ID NO 23
<211> LENGTH: 36
<212> TYPE: DNA
<213> ORGANISM: Artificial Sequence
<220> FEATURE:
<223> OTHER INFORMATION: Probe

<400> SEQUENCE: 23
acagaatatt tttccataat tttcttgtat agcagt                                  36

<210> SEQ ID NO 24
<211> LENGTH: 29
<212> TYPE: DNA
<213> ORGANISM: Artificial Sequence
<220> FEATURE:
<223> OTHER INFORMATION: Probe
```

```
<400> SEQUENCE: 24
acattttaaa ggccaaggat tagctgtac                                              29

<210> SEQ ID NO 25
<211> LENGTH: 28
<212> TYPE: DNA
<213> ORGANISM: Artificial Sequence
<220> FEATURE:
<223> OTHER INFORMATION: Probe

<400> SEQUENCE: 25
acgcaacctt ctttcttttc ctcttcac                                               28

<210> SEQ ID NO 26
<211> LENGTH: 33
<212> TYPE: DNA
<213> ORGANISM: Artificial Sequence
<220> FEATURE:
<223> OTHER INFORMATION: Probe

<400> SEQUENCE: 26
tatggcttct ttttaagcta tcctttactt agt                                         33

<210> SEQ ID NO 27
<211> LENGTH: 33
<212> TYPE: DNA
<213> ORGANISM: Artificial Sequence
<220> FEATURE:
<223> OTHER INFORMATION: Primer/probe

<400> SEQUENCE: 27
ctttgctatt tacaccacaa aggaaaaagc tgc                                         33

<210> SEQ ID NO 28
<211> LENGTH: 29
<212> TYPE: DNA
<213> ORGANISM: Artificial Sequence
<220> FEATURE:
<223> OTHER INFORMATION: Primer/probe

<400> SEQUENCE: 28
aatagcagac actctatgcc tgtgtggag                                              29

<210> SEQ ID NO 29
<211> LENGTH: 78
<212> TYPE: DNA
<213> ORGANISM: Artificial Sequence
<220> FEATURE:
<223> OTHER INFORMATION: Primer-probe complex

<400> SEQUENCE: 29
aacccaccca gaatattttt ccataatttt cttgtatagc agtgggtggg tttatttaca            60
ccacaaagga aaaagctg                                                          78
```

SEQUENCES AND THEIR USE FOR DETECTION AND CHARACTERIZATION OF *E. COLI* O157:H7

CROSS-REFERENCE TO RELATED APPLICATION

This application claims the benefit of U.S. Provisional Application No. 61/227,622, filed Jul. 22, 2009, which is incorporated by reference herein in its entirety.

GOVERNMENT INTERESTS

This invention was made under a Cooperative Research and Development Agreement with the Agricultural Research Service (Agreement No. 58-3K95-8-1254-M). The government may have certain rights in this invention.

FIELD OF INVENTION

The field of invention relates to methods for detection and characterization of *Escherichia coli* bacteria serotype O157:H7 based on the presence of nucleic acid sequences, preferably PCR-based methods for detection, and to oligonucleotide molecules and reagents and kits useful therefor.

BACKGROUND OF INVENTION

*Escherichia coli* (*E. coli*) is a gram-negative, rod-shaped bacterium. Although most strains of *E. coli* are benign and are found as normal intestinal flora of humans and other animals, some strains are pathogenic and can lead to sometimes-fatal disease. Different strains of pathogenic *E. coli* differ in their epidemiology, clinical course and potential for causing outbreaks of disease. Passage of disease is generally through the fecal/oral route.

Pathogenicity has been linked to several serotypes, as defined by O and H antigens. Different pathogenic serotypes are associated with different clinical disease courses and have associated with them different levels of concern from the standpoint of public health. Several outbreaks of disease have been tracked to food and water borne sources of pathogenic *E. coli*.

One serotype of *E. coli* in particular, serotype O157:H7, has been associated with several food and water borne outbreaks and is regulated as an adulterant in ground beef by the U.S. Department of Agriculture (USDA) with a zero tolerance standard. This serotype of *E. coli* is believed to have arisen from an O55:H7 parent strain, which then switched from O55 to O157 upon the transfer into the progenitor O55:H7 genome of the large virulence plasmid pO157, which contained the O157-rfb gene cluster as well as some additional genetic information (see, e.g., Lukas M. Wick, et al., *Evolution of Genomic Content in the Stepwise Emergence of Escherichia coli O157:H7*, Journal of Bacteriology 187:1783-91 (2005)).

Since *E. coli* is ubiquitous, and since serotype O157:H7 is highly pathogenic and tightly regulated, the ability to specifically detect and characterize *E. coli* serotype O157:H7 in a sample, even in the presence of other *E. coli* serotypes, is useful.

It is desirable, therefore, to have a test for the accurate detection and characterization of *E. coli* O157:H7 in a sample.

SUMMARY OF INVENTION

One aspect is for a method for detecting the presence of *E. coli* O157:H7 in a sample, said sample comprising nucleic acids, said method comprising:

(a) providing a reaction mixture comprising suitable primer pairs for amplification of at least a portion of
  (i) one or more *E. coli* O157:H7 genomic DNA regions within the pO157 portion of the *E. coli* O157:H7 genome, and
  (ii) one or more *E. coli* O157:H7 genomic DNA regions outside the pO157 portion of the *E. coli* O157:H7 genome;
(b) performing PCR amplification of said nucleic acids of said sample using the reaction mixture of step (a); and
(c) detecting the amplification of step (b), whereby a positive detection of amplification indicates the presence of *E. coli* O157:H7 in the sample.

Another aspect is for an isolated polynucleotide comprising SEQ ID NO:4, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:24, SEQ ID NO:25, or SEQ ID NO:26.

A further aspect is for a replication composition for use in performance of PCR, comprising:
(a) a primer pair comprising nucleic acid sequences SEQ ID NO:4 and SEQ ID NO:5;
(b) one or more primer pairs comprising nucleic acid sequences selected from the group consisting of:
  (i) SEQ ID NO:10 and SEQ ID NO:12;
  (ii) SEQ ID NO:15 and SEQ ID NO:16; and
  (iii) a combination thereof; and
(b) thermostable DNA polymerase.

An additional aspect is for a replication composition for use in performance of PCR, comprising:
(a) a primer pair comprising nucleic acid sequences SEQ ID NO:5 and SEQ ID NO:6;
(b) one or more primer pairs comprising nucleic acid sequences selected from the group consisting of:
  (i) SEQ ID NO:12 and SEQ ID NO:13;
  (ii) SEQ ID NO:16 and SEQ ID NO:17; and
  (iii) a combination thereof; and
(b) thermostable DNA polymerase.

Other objects and advantages will become apparent to those skilled in the art upon reference to the detailed description that hereinafter follows.

SUMMARY OF THE SEQUENCES

SEQ ID NO:1 is the nucleotide sequence of a region outside the pO157 portion of *E. coli* serotype O157:H7 genome, the detection of which specifically shows the presence of that bacterial serotype. SEQ ID NO:1 or its reverse complementary sequence is bounded by, contains or contains binding sites for, and can be amplified by the use of SEQ ID NO:5 or SEQ ID NO:8 in conjunction with SEQ ID NO:4 or SEQ ID NO:6. This region also contains a binding site for the oligonucleotide SEQ ID NO:7 or SEQ ID NO:9.

SEQ ID NO:2 is the nucleotide sequence of a region within the pO157 portion of *E. coli* serotype O157:H7 genome, the detection of which specifically shows the presence of that bacterial serotype. SEQ ID NO:2 or its reverse complementary sequence is bounded by, contains or contains binding sites for, and can be amplified by the use of SEQ ID NO:12 in conjunction with SEQ ID NO:10 or SEQ ID NO:13, and also contains a binding site for probe SEQ ID NO:14.

SEQ ID NO:3 is the nucleotide sequence of a region within the pO157 portion of *E. coli* serotype O157:H7 genome, the detection of which specifically shows the presence of that bacterial serotype. SEQ ID NO:3 or its reverse complementary sequence is bounded by, contains or contains binding sites for, and can be amplified by the use of SEQ ID NO:16 in conjunction with SEQ ID NO:15, SEQ ID NO:17, or SEQ ID NO:19, and also contains a binding site for SEQ ID NO:18 and SEQ ID NO:20.

SEQ ID NO:4 is the nucleotide sequence of a primer-probe complex for detection of E. coli serotype O157:H7, specifically the region of the genome identified by SEQ ID NO:1. The 3' portion of this primer-probe complex is capable of hybridizing to SEQ ID NO:1 or its reverse complementary sequence and acting as a 5' primer, such as during an amplification reaction that also employs an appropriate 3' primer, such as SEQ ID NO:5. The 5' portion of this primer-probe complex contains a segment capable of hybridizing to SEQ ID NO:1 or its reverse complementary sequence at a location downstream (i.e., in the 3' direction) from the binding location of the primer portion of the primer-probe complex, and upstream (i.e., in the 5' direction) of the binding location of any 3' primer that is employed in an amplification reaction. The 5' portion of this primer-probe complex also contains two self-complementary segments (nucleotides 1-9 and 38-46) capable of self-hybridizing to form a stem-loop structure. The 5' and 3' portions of this primer-probe complex are separated by a non-amplifiable linker between nucleotide 46 ("T") and nucleotide 47 ("G"). This non-amplifiable linker is capable of blocking elongation of a complementary strand to this primer-probe complex.

SEQ ID NO:5 is the nucleotide sequence of a region of the genome of E. coli serotype O157:H7 capable for use as a probe or primer in detection of the presence of SEQ ID NO:1 and subsequent detection of the presence of E. coli O157:H7. This sequence is preferably used as a primer that will specifically amplify DNA of that bacterial serotype in a polymerase chain reaction with bacterial DNA when used as a 3' primer with an appropriate 5' primer, such as SEQ ID NO:4 or SEQ ID NO:6.

SEQ ID NO:6 is the nucleotide sequence of a region of the genome of E. coli serotype O157:H7 capable for use as a probe or primer in detection of the presence of SEQ ID NO:1 and subsequent detection of the presence of E. coli O157:H7. This sequence is preferably used as a primer that will specifically amplify DNA of that bacterial serotype in a polymerase chain reaction with bacterial DNA when used as a 5' primer with an appropriate 3' primer, such as SEQ ID NO:5.

SEQ ID NO:7 is the nucleotide sequence of a region of the genome of E. coli serotype O157:H7 capable for use as a probe or primer in detection of the presence of SEQ ID NO:1 and subsequent detection of the presence of E. coli O157:H7. This sequence is preferably used as a probe that will hybridize to and allow detection of the DNA of that bacterial serotype in a polymerase chain reaction with bacterial DNA when used with an appropriate 5' primer, such as SEQ ID NO:6, and an appropriate 3' primer, such as SEQ ID NO:5.

SEQ ID NO:8 is the nucleotide sequence of a region of the genome of E. coli serotype O157:H7 capable for use as a probe or primer in detection of the presence of SEQ ID NO:1 and subsequent detection of the presence of E. coli O157:H7. This sequence is preferably used as a primer that will specifically amplify DNA of that bacterial serotype in a polymerase chain reaction with bacterial DNA when used as a 3' primer with an appropriate 5' primer, such as SEQ ID NO:4 or SEQ ID NO:6.

SEQ ID NO:9 is the nucleotide sequence of a region of the genome of E. coli serotype O157:H7 capable for use as a probe or primer in detection of the presence of SEQ ID NO:1 and subsequent detection of the presence of E. coli O157:H7. This sequence is preferably used as a primer that will specifically amplify DNA of that bacterial serotype in a polymerase chain reaction with bacterial DNA when used as a 5' primer with an appropriate 3' primer.

SEQ ID NO:10 is the nucleotide sequence of a primer-probe complex for detection of E. coli serotype O157:H7, specifically the region of the genome identified by SEQ ID NO:2. The 3' portion of this primer-probe complex is capable of hybridizing to SEQ ID NO:2 or its reverse complement sequence and acting as a 5' primer, such as during an amplification reaction that also employs an appropriate 3' primer, such as SEQ ID NO:12. The 5' portion of this primer-probe complex contains a segment capable of hybridizing to SEQ ID NO:2 or its reverse complement sequence at a location downstream (i.e., in the 3' direction) from the binding location of the primer portion of the primer-probe complex, and preferably upstream (i.e., in the 5' direction) of the binding location of any 3' primer that is employed in an amplification reaction. The 5' and 3' portions of this primer-probe complex are separated by a non-amplifiable linker between nucleotide 34 ("G") and nucleotide 35 ("C"). This non-amplifiable linker is capable of blocking elongation of a complementary strand to this primer-probe complex.

SEQ ID NO:11 is a blocking oligonucleotide capable of hybridizing to the probe portion of the SEQ ID NO:10 probe-primer complex.

SEQ ID NO:12 is the nucleotide sequence of a region of the genome of E. coli serotype O157:H7 capable for use as a probe or primer in detection of the presence of SEQ ID NO:2 and subsequent detection of the presence of E. coli O157:H7. This sequence is preferably used as a primer that will specifically amplify DNA of that bacterial serotype in a polymerase chain reaction with bacterial DNA when used as a 3' primer with an appropriate 5' primer, such as SEQ ID NO:10 or SEQ ID NO:13.

SEQ ID NO:13 is the nucleotide sequence of a region of the genome of E. coli serotype O157:H7 capable for use as a probe or primer in detection of the presence of SEQ ID NO:2 and subsequent detection of the presence of E. coli O157:H7. This sequence is preferably used as a primer that will specifically amplify DNA of that bacterial serotype in a polymerase chain reaction with bacterial DNA when used as a 5' primer with an appropriate 3' primer, such as SEQ ID NO:12.

SEQ ID NO:14 is the nucleotide sequence of a region of the genome of E. coli serotype O157:H7 capable for use as a probe or primer in detection of the presence of SEQ ID NO:2 and subsequent detection of the presence of E. coli O157:H7. This sequence is preferably used as a probe that will hybridize to and allow detection of the DNA of that bacterial serotype in a polymerase chain reaction with bacterial DNA when used with an appropriate 5' primer, such as SEQ ID NO:13, and an appropriate 3' primer, such as SEQ ID NO:12.

SEQ ID NO:15 is the nucleotide sequence of a primer-probe complex for detection of E. coli serotype O157:H7, specifically the region of the genome identified by SEQ ID NO:3. The 3' portion of this primer-probe complex is capable of hybridizing to SEQ ID NO:3 or its reverse complement sequence and acting as a 5' primer, such as during an amplification reaction that also employs an appropriate 3' primer, such as SEQ ID NO:16. The 5' portion of this primer-probe complex contains a segment capable of hybridizing to SEQ ID NO:3 or its reverse complement sequence at a location downstream (i.e., in the 3' direction)

from the binding location of the primer portion of the primer-probe complex, and preferably upstream (i.e., in the 5' direction) of the binding location of any 3' primer that is employed in an amplification reaction. The 5' portion of this primer-probe complex also contains two self-complementary segments (nucleotides 1-9 and 37-45) capable of self-hybridizing to form a stem-loop structure. The 5' and 3' portions of this primer-probe complex are separated by a non-amplifiable linker between nucleotide 45 ("T") and nucleotide 46 ("A"). This non-amplifiable linker is capable of blocking elongation of a complementary strand to this primer-probe complex.

SEQ ID NO:16 is the nucleotide sequence of a region of the genome of E. coli serotype O157:H7 capable for use as a probe or primer in detection of the presence of SEQ ID NO:3 and subsequent detection of the presence of E. coli O157:H7. This sequence is preferably used as a primer that will specifically amplify DNA of that bacterial serotype in a polymerase chain reaction with bacterial DNA when used as a 3' primer with an appropriate 5' primer, such as SEQ ID NO:15 or SEQ ID NO:17.

SEQ ID NO:17 is the nucleotide sequence of a region of the genome of E. coli serotype O157:H7 capable for use as a probe or primer in detection of the presence of SEQ ID NO:3 and subsequent detection of the presence of E. coli O157:H7. This sequence is preferably used as a primer that will specifically amplify DNA of that bacterial serotype in a polymerase chain reaction with bacterial DNA when used as a 5' primer with an appropriate 3' primer, such as SEQ ID NO:16.

SEQ ID NO:18 is the nucleotide sequence of a region of the genome of E. coli serotype O157:H7 capable for use as a probe or primer in detection of the presence of SEQ ID NO:3 and subsequent detection of the presence of E. coli O157:H7. This sequence is preferably used as a probe that will hybridize to and allow detection of the DNA of that bacterial serotype in a polymerase chain reaction with bacterial DNA when used with an appropriate 5' primer, such as SEQ ID NO:17, and an appropriate 3' primer, such as SEQ ID NO:16.

SEQ ID NO:19 is the nucleotide sequence of a region of the genome of E. coli serotype O157:H7 capable for use as a probe or primer in detection of the presence of SEQ ID NO:3 and subsequent detection of the presence of E. coli O157:H7. This sequence is preferably used as a primer that will specifically amplify DNA of that bacterial serotype in a polymerase chain reaction with bacterial DNA when used as a 5' primer with an appropriate 3' primer, such as SEQ ID NO: 16.

SEQ ID NO:20 is the nucleotide sequence of a region of the genome of E. coli serotype O157:H7 capable for use as a probe or primer in detection of the presence of SEQ ID NO:3 and subsequent detection of the presence of E. coli O157:H7. This sequence is preferably used as a primer that will specifically amplify DNA of that bacterial serotype in a polymerase chain reaction with bacterial DNA when used as a 3' primer with an appropriate 5' primer.

SEQ ID NO:21 is the nucleotide sequence capable for use as an internal control primer. This sequence is preferably used as a primer that will specifically amplify DNA in a polymerase chain reaction with a control template DNA when used as a 5' primer with an appropriate 3' primer, such as SEQ ID NO:22.

SEQ ID NO:22 is the nucleotide sequence capable for use as an internal control primer. This sequence is preferably used as a primer that will specifically amplify DNA in a polymerase chain reaction with a control template DNA when used as a 3' primer with an appropriate 5' primer, such as SEQ ID NO:21.

SEQ ID NO:23 is the nucleotide sequence of an internal control Taqman® probe.

SEQ ID NO:24 is the nucleotide sequence of a Taqman® probe for detection of E. coli serotype O157:H7, specifically the region of the genome identified by SEQ ID NO:2.

SEQ ID NO:25 is the nucleotide sequence of a Taqman® probe for detection of E. coli serotype O157:H7, specifically the region of the genome identified by SEQ ID NO:1.

SEQ ID NO:26 is the nucleotide sequence of a Taqman® probe for detection of E. coli serotype O157:H7, specifically the region of the genome identified by SEQ ID NO:3.

SEQ ID NO:27 is the nucleotide sequence capable for use as an internal control primer. This sequence is preferably used as a primer that will specifically amplify DNA in a polymerase chain reaction with a control template DNA when used as a 5' primer with an appropriate 3' primer, such as SEQ ID NO:28.

SEQ ID NO:28 is the nucleotide sequence capable for use as an internal control primer. This sequence is preferably used as a primer that will specifically amplify DNA in a polymerase chain reaction with a control template DNA when used as a 3' primer with an appropriate 5' primer, such as SEQ ID NO:27.

SEQ ID NO:29 is the nucleotide sequence of an internal control scorpion probe.

The sequences conform with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

DETAILED DESCRIPTION OF PREFERRED EMBODIMENTS

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

DEFINITIONS

In this disclosure, a number of terms and abbreviations are used. The following definitions are provided.

As used herein, the term "about" or "approximately" means within 20%, preferably within 10%, and more preferably within 5% of a given value or range.

The term "comprising" is intended to include embodiments encompassed by the terms "consisting essentially of"

and "consisting of". Similarly, the term "consisting essentially of" is intended to include embodiments encompassed by the term "consisting of".

The term "pO157 portion" refers to the area of the *E. coli* O157:H7 genome identified, for example, in Lukas M. Wick, et al., *Evolution of Genomic Content in the Stepwise Emergence of Escherichia coli O157:H7*, Journal of Bacteriology 187:1783-91 (2005), as being divergent from the O55:H7 progenitor strain and as having been transferred into the progenitor strain to create the O157:H7 *E. coli* serotype. This region includes, among other things, the O157-rfb gene cluster, colonic acid biosynthesis genes, and putative type-1 fimbrial protein genes.

"Polymerase chain reaction" is abbreviated PCR.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "polynucleotide", "polynucleotide sequence", "nucleic acid sequence", and "nucleic acid fragment" are used interchangeably herein. These terms encompass nucleotide sequences and the like. A polynucleotide may be a polymer of RNA or DNA that is single- or double-stranded, that optionally contains synthetic, non-natural, or altered nucleotide bases. A polynucleotide in the form of a polymer of DNA may be comprised of one or more strands of cDNA, genomic DNA, synthetic DNA, or mixtures thereof.

The term "amplification product" refers to nucleic acid fragments produced during a primer-directed amplification reaction. Typical methods of primer-directed amplification include polymerase chain reaction (PCR), ligase chain reaction (LCR), or strand displacement amplification (SDA). If PCR methodology is selected, the replication composition may comprise the components for nucleic acid replication, for example: nucleotide triphosphates, two (or more) primers with appropriate sequences, thermostable polymerase, buffers, solutes, and proteins. These reagents and details describing procedures for their use in amplifying nucleic acids are provided in U.S. Pat. No. 4,683,202 (1987, Mullis, et al.) and U.S. Pat. No. 4,683,195 (1986, Mullis, et al.). If LCR methodology is selected, then the nucleic acid replication compositions may comprise, for example: a thermostable ligase (e.g., *Thermus aquaticus* ligase), two sets of adjacent oligonucleotides (wherein one member of each set is complementary to each of the target strands), Tris-HCl buffer, KCl, EDTA, NAD, dithiothreitol, and salmon sperm DNA. See, for example, Tabor et al., *Proc. Natl. Acad. Sci. U.S.A.* 82:1074-1078 (1985).

The term "primer" refers to an oligonucleotide (synthetic or occurring naturally) that is capable of acting as a point of initiation of nucleic acid synthesis or replication along a complementary strand when placed under conditions in which synthesis of a complementary strand is catalyzed by a polymerase. A primer can further contain a detectable label, for example a 5' end label.

The term "probe" refers to an oligonucleotide (synthetic or occurring naturally) that is complementary (though not necessarily fully complementary) to a polynucleotide of interest and forms a duplexed structure by hybridization with at least one strand of the polynucleotide of interest. A probe or primer-probe complex can further contain a detectable label.

A probe can either be an independent entity or complexed with or otherwise attached to a primer, such as where a probe is connected via its 3' terminus to a primer's 5' terminus through a linker, which may be a nucleotide or non-nucleotide linker and which may be a non-amplifiable linker, such as a hexethylene glycol (HEG) or 18-carbon linker. In such a case, this would be termed a "primer-probe complex." One example of such a primer-probe complex can be found in U.S. Pat. No. 6,326,145, incorporated herein by reference in its entirety, which are frequently referred to as "Scorpion probes" or "Scorpion primers."

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin, or haptens), and the like. A detectable label can also include a combination of a reporter and a quencher.

The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter.

As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

Preferably, the reporter may be selected from fluorescent organic dyes modified with a suitable linking group for attachment to the oligonucleotide, such as to the terminal 3' carbon or terminal 5' carbon. The quencher may also be selected from organic dyes, which may or may not be fluorescent, depending on the embodiment of the present invention. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radioactively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, Handbook of Fluorescence Spectra of Aromatic Molecules, 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland, Handbook of Fluorescent Probes and Research Chemicals, Molecular Probes of Eugene, Oreg., 1992, the content of which is incorporated herein by reference.

Preferred reporter-quencher pairs may be selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another preferred group of fluorescent compounds for use as reporters are the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like.

Most preferably, the reporters and quenchers are selected from fluorescein and rhodamine dyes. These dyes and appropriate linking methodologies for attachment to oligonucleotides are well known in the art.

Suitable examples of quenchers may be selected from 6-carboxy-tetramethyl-rhodamine, 4-(4-dimethylaminophenylazo)benzoic acid (DABYL), tetramethylrhodamine (TAMRA), BHQ-0™, BHQ-1™ BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like.

One example of a probe which contains a reporter and a quencher is a Scorpion probe in either a unimolecular or bimolecular conformation. In a unimolecular Scorpion, the probe portion of the primer-probe complex is flanked by self-complementary regions which allow the probe to form into a stem-loop structure when the probe is unbound from its target DNA. Examples of such self-complementary regions can be found in SEQ ID NO:4 and SEQ ID NO:15. Further, in a unimolecular Scorpion, a reporter is typically attached at or near one of the self-complementary regions, such as at the 5' terminus of the Scorpion probe, and a quencher is attached at or near the other self-complementary region, such as immediately 5' to the non-amplifiable linker, such that the quencher is in sufficiently close proximity to the reporter to cause quenching when the probe is in its stem-loop conformation. In a bimolecular Scorpion, self-complementary flanking regions are not typically employed, but rather a separate "blocking oligonucleotide" is employed in conjunction with the Scorpion probe. This blocking oligonucleotide is capable of hybridizing to the probe region of the Scorpion probe when the probe is unbound from its target DNA. An example of a bimolecular Scorpion pair is SEQ ID NO:10 (the Scorpion probe) and SEQ ID NO:11 (the blocking oligonucleotide). Further, in a bimolecular Scorpion, the reporter is typically attached to the probe region of the Scorpion probe, such as at the 5' terminus of the Scorpion probe, while the quencher is attached to the blocking oligonucleotide, such as at the 3' terminus of the blocking oligonucleotide, such that the quencher is in sufficiently close proximity to the reporter to cause quenching when the probe is unbound from its target DNA and is instead hybridized to the blocking oligonucleotide.

Another example of a probe which contains a reporter and a quencher is a probe that is to be used in a 5'-exonuclease assay, such as the Taqman® real-time PCR technique. In this context, the oligonucleotide probe will have a sufficient number of phosphodiester linkages adjacent to its 5' end so that the 5' to 3' nuclease activity employed can efficiently degrade the bound probe to separate the reporters and quenchers. Yet another example of a probe which contains a reporter and quencher is a Molecular Beacon type probe, which contains a probe region flanked by self-complementary regions that allow the probe to form a stem-loop structure when unbound from the probe's target sequence. Such probes typically have a reporter attached at or near one terminus and a quencher attached at or near the other terminus such that the quencher is in sufficiently close proximity to the reporter to cause quenching when the probe is in its unbound, and thus stem-loop, form.

The term "replication inhibitor moiety" refers to any atom, molecule or chemical group that is attached to the 3' terminal hydroxyl group of an oligonucleotide that will block the initiation of chain extension for replication of a nucleic acid strand. Examples include, but are not limited to: 3'-deoxynucleotides (e.g., cordycepin), dideoxynucleotides, phosphate, ligands (e.g., biotin and dinitrophenol), reporter molecules (e.g., fluorescein and rhodamine), carbon chains (e.g., propanol), a mismatched nucleotide or polynucleotide, or peptide nucleic acid units. The term "non-participatory" refers to the lack of participation of a probe or primer in a reaction for the amplification of a nucleic acid molecule. Specifically a non-participatory probe or primer is one that will not serve as a substrate for, or be extended by, a DNA or RNA polymerase. A "non-participatory probe" is inherently incapable of being chain extended by a polymerase. It may or may not have a replication inhibitor moiety.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, for example, in Sambrook, J., Fritsch, E. F. and Maniatis, T., *Molecular Cloning: A Laboratory Manual,* 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. For preliminary screening for homologous nucleic acids, low stringency hybridization conditions, corresponding to a Tm of 55° C., can be used, e.g., 5×SSC, 0.1% SDS, 0.25% milk, and no formamide; or 30% formamide, 5×SSC, 0.5% SDS. Moderate stringency hybridization conditions correspond to a higher Tm, e.g., 40% formamide, with 5× or 6×SSC. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one preferred embodiment, the length for a hybridizable nucleic acid is at least about 10 nucleotides. More preferably a minimum length for a hybridizable nucleic acid is at least about 11 nucleotides, at least about 12 nucleotides, at least about 13 nucleotides, at least about 14 nucleotides, at least about 15 nucleotides, at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, or, most preferably, at least 30 nucleotides. Furthermore, the skilled artisan will recognize that the temperature and wash solution salt concentration may be adjusted as necessary according to factors such as length of the probe.

Standard recombinant DNA and molecular cloning techniques used here are well known in the art and are described by, e.g., Sambrook et al. (supra); and by Ausubel, F. M. et al., *Current Protocols in Molecular Biology*, published by Greene Publishing Assoc. and Wiley-Interscience (1987).

Genome Detection Regions

As discussed above, *E. coli* O157:H7 came about via the transfer of the pO157 plasmid into the O55:H7 progenitor strain. Thus, *E. coli* O157:H7 possesses a pO157 portion within the bacterial genome. It has been found that the detection of a combination of regions both within and outside this pO157 portion of the *E. coli* O157:H7 genome produces a sensitive and accurate method of detecting *E. coli* O157:H7, even in a background of other serotypes of *E. coli*.

The present invention therefore relates to detection and identification of *E. coli* O157:H7 through the detection of the presence of one or more *E. coli* O157:H7 genomic DNA regions within the pO157 portion of the genome in conjunction with the detection of the presence of one or more *E. coli* O157:H7 genomic DNA regions outside the pO157 portion of the genome. Preferably detection of *E. coli* O157:H7 is accomplished through the use of methods for detecting the presence of SEQ ID NO:1 in conjunction with one or more, more preferably both, of SEQ ID NOs: 2 and 3. The present detection method finds utility in detection of *E. coli* O157:H7 in any type of sample, for example in appropriate samples for food testing, environmental testing, or human or animal diagnostic testing. While examples of suitable methods for detecting these regions are included herein, it is to be understood that the invention is not limited to the methods described. Rather any suitable method can be employed to detect these DNA regions and subsequently the *E. coli* itself.

Oligonucleotides

Oligonucleotides have been developed for the detection of the *E. coli* DNA regions SEQ ID NOs: 1-3 and the subsequent detection and identification of *E. coli* serotype O157:H7. Oligonucleotides of the instant invention are set forth in SEQ ID NOs: 4-20 and 24-26.

Oligonucleotides of the instant invention may be used as primers for PCR amplification. Preferred oligonucleotides for use as primers are SEQ ID NO:4, SEQ ID NO:5, SEQ ID NO:6, SEQ ID NO:8, SEQ ID NO:9, SEQ ID NO:10, SEQ ID NO:12, SEQ ID NO:13, SEQ ID NO:15, SEQ ID NO:16, SEQ ID NO:17, SEQ ID NO:19, and SEQ ID NO:20. Particularly preferred primer pairs and their corresponding targets, blocking oligonucleotides, and probes are shown in Table 1.

TABLE 1

| Target DNA Region | 5' (Forward) Primer/Primer-Probe Complex | Blocking Oligo-nucleotide | 3' (Reverse) Primer | Probe |
|---|---|---|---|---|
| SEQ ID NO: 1 | SEQ ID NO: 4 | N/A | SEQ ID NO: 5 | N/A |
| SEQ ID NO: 1 | SEQ ID NO: 6 | N/A | SEQ ID NO: 5 | SEQ ID NO: 7 |
| SEQ ID NO: 2 | SEQ ID NO: 10 | SEQ ID NO: 11 | SEQ ID NO: 12 | N/A |
| SEQ ID NO: 2 | SEQ ID NO: 13 | N/A | SEQ ID NO: 12 | SEQ ID NO: 14 |
| SEQ ID NO: 3 | SEQ ID NO: 15 | N/A | SEQ ID NO: 16 | N/A |
| SEQ ID NO: 3 | SEQ ID NO: 17 | N/A | SEQ ID NO: 16 | SEQ ID NO: 18 |

Each of these primers and probes was designed based on sequence analysis of its corresponding region of the *E. coli* O157:H7 genome. Primer design was not aided by any software program.

These oligonucleotide primers may also be useful for other nucleic acid amplification methods such as the ligase chain reaction (LCR) (Backman et al., 1989, EP 0 320 308; Carrino et al., 1995, *J. Microbiol. Methods* 23: 3-20); nucleic acid sequence-based amplification (NASBA), (Carrino et al., 1995, supra); and self-sustained sequence replication (3SR) and 'Q replicase amplification' (Pfeffer et al., 1995 *Veterinary Res. Comm.* 19: 375-407).

The oligonucleotide primers of the present invention can also contain a detectable label, for example a 5' end label.

In addition, oligonucleotides of the present invention also may be used as hybridization probes. Preferred hybridization probes are SEQ ID NO:4, SEQ ID NO:7, SEQ ID NO:10, SEQ ID NO:14, SEQ ID NO:15, SEQ ID NO:18, SEQ ID NO:24, SEQ ID NO:25, and SEQ ID NO:26. Hybridization using DNA probes has been frequently used for the detection of pathogens in food, clinical and environmental samples, and the methodologies are generally known to one skilled in the art. It is generally recognized that the degree of sensitivity and specificity of probe hybridization is lower than that achieved through the previously described amplification techniques. The nucleic acid probes of the present invention can also possess a detectable label, such as a reporter-quencher combination as are employed in Scorpion probe assays or in 5'-exonuclease detection assays, such as the Taqman® assay.

The 3' terminal nucleotide of the nucleic acid probe may be rendered incapable of extension by a nucleic acid polymerase in one embodiment of the invention. Such blocking may be carried out, for example by the attachment of a replication inhibitor moiety, such as a reporter or quencher, to the terminal 3' carbon of the nucleic acid probe by a linking moiety, or by making the 3'-terminal nucleotide a dideoxynucleotide. Alternatively, the 3' end of the nucleic acid probe may be rendered impervious to the 3' to 5' extension activity of a polymerase by incorporating one or more modified internucleotide linkages onto the 3' end of the oligonucleotide. Minimally, the 3' terminal internucleotide linkage must be modified, however, additional internucleotide linkages may be modified. Internucleotide modifications which prevent elongation from the 3' end of the nucleic acid probe and/or which block the 3' to 5' exonuclease activity of the DNA polymerase during PCR may include phosphorothioate linkages, methylphosphonate linkages, boranophosphate linkages, and other similar polymerase-resistant internucleotide linkages. An alternative method to block 3' extension of the probe is to form an adduct at the 3' end of the probe using mitomycin C or other like antitumor antibiotics such as described in Basu et al., Biochemistry 32:4708-4718, 1993. Thus, the precise mechanism by which the 3' end of the nucleic acid probe is protected from cleavage is not essential so long as the quencher is not cleaved from the nucleic acid probe.

A nucleic acid probe sequence can also optionally be employed with the primer sequence pairs of the present invention in an amplification based detection technique, such as in the 3'-exonuclease assay. Preferred primer/probe combinations are indicated in Table 1.

Some oligonucleotides of the present invention contain both primer and probe regions, and thus can be employed as a primer-probe complex in an appropriate assay, such as a Scorpion probe assay. Examples of such primer-probe complexes of the current invention include SEQ ID NO:4, SEQ ID NO:10, and SEQ ID NO:15. These primer probe complexes of the instant invention contain a non-amplifiable linker that connects the 3' terminus of the probe region to the 5' terminus of the primer region. This non-amplifiable linker stops extension of a complementary strand from proceeding into the probe region of the primer-probe complex. Examples of such non-amplifiable linkages include hexethylene glycol (HEG) and, preferably, 18-carbon linkers. Primer-probe complexes of the present invention can also contain a self-complementary region that allows the primer-probe complex to form a stem-loop structure when the probe is unbound from its target DNA, which may be useful, for example, in bringing the reporter and quencher into sufficiently close proximity to one another to cause the reporter signal to be quenched. Examples of such primer-probe complexes with self-complementary regions include SEQ ID NO:4 and SEQ ID NO:15. Preferably, SEQ ID NO:4 is 5' end-labeled with a Quasar670 reporter and also possesses a BHQ2 quencher at or near the 3' end of the probe region of this primer-probe complex (e.g., attached to nucleotide 46). Preferably, SEQ ID NO:15 is 5' end-labeled with a Calfluor Orange 560 reporter and also possesses a BHQ1 quencher at or near the 3' end of the probe region of this primer-probe complex (e.g., attached to nucleotide 45). In some instances, a blocking oligonucleotide can be employed with a primer-probe complex, which blocking oligonucleotide is capable of hybridizing to the probe region of the primer-probe complex when the probe region is unbound from its target DNA. If the reporter is attached to the primer-probe complex and the quencher is attached to the blocking oligonucleotide, this can bring the reporter and quencher into sufficiently close proximity to one another to allow quenching to occur. For example, SEQ ID NO:11 is a blocking oligonucleotide capable of hybridizing to the primer-probe complex SEQ ID NO:10. Preferably, SEQ ID NO:10 is 3' end-labeled with a 6FAM reporter while SEQ ID NO:11 is 5' end-labeled with a BHQ1 quencher.

Assay Methods

Detection of the *E. coli* O157:H7 genomic DNA regions identified by SEQ ID NOs: 1-3, and subsequent detection of the presence of *E. coli* O157:H7 itself, may be accomplished in any suitable manner. Preferred methods are primer-directed amplification methods and nucleic acid hybridization methods. These methods may be used to detect *E. coli* O157:H7 in a sample that is either a complex matrix or a purified culture, e.g., from an animal, environmental, or food source suspected of contamination.

A preferred embodiment of the instant invention comprises (1) culturing a complex sample mixture in a non-selective growth media to resuscitate the target bacteria, (2) releasing total target bacterial DNA, and (3) subjecting the total DNA to an amplification protocol with a primer pair of the invention and optionally with a nucleic acid probe comprising a detectable label.

Primer-Directed Amplification Assay Methods

A variety of primer-directed nucleic acid amplification methods are known in the art which can be employed in the present invention, including thermal cycling methods (e.g., PCR, RT-PCR, and LCR), as well as isothermal methods and strand displacement amplification (SDA). The preferred method is PCR. In one preferred embodiment, the primer pairs listed in Table 1 may be used as primers for use in primer-directed nucleic acid amplification for the detection of SEQ ID NOs: 1-3 and subsequently detection and identification of *E. coli* O157:H7.

Sample Preparation:

The oligonucleotides and methods according to the instant invention may be used directly with any suitable clinical or environmental samples, without any need for sample preparation. In order to achieve higher sensitivity, and in situations where time is not a limiting factor, it is preferred that the samples be pre-treated and that pre-amplification enrichment is performed.

The minimum industry standard for the detection of food-borne bacterial pathogens is a method that will reliably detect the presence of one pathogen cell in 25 g of food matrix as described in Andrews et al., 1984, "Food Sample and Preparation of Sample Homogenate", Chapter 1 in *Bacteriological Analytical Manual,* 8th Edition, Revision A, Association of Official Analytical Chemists, Arlington, Va. In order to satisfy this stringent criterion, enrichment methods and media have been developed to enhance the growth of the target pathogen cell in order to facilitate its detection by biochemical, immunological or nucleic acid hybridization means. Typical enrichment procedures employ media that will enhance the growth and health of the target bacteria and also inhibit the growth of any background or non-target microorganisms present. For example, the USDA has set forth a protocol for enrichment of samples of ground beef to be tested for pathogenic *E. coli* (U.S. Food and Drug Administration, Bacterial Analytical Manual).

Selective media have been developed for a variety of bacterial pathogens and one of skill in the art will know to select a medium appropriate for the particular organism to be enriched, e.g. *E. coli* O157:H7. A general discussion and recipes of non-selective media are described in the FDA Bacteriological Analytical Manual. (1998) published and distributed by the Association of Analytical Chemists, Suite 400, 2200 Wilson Blvd, Arlington, Va. 22201-3301.

After selective growth, a sample of the complex mixtures is removed for further analysis. This sampling procedure may be accomplished by a variety of means well known to those skilled in the art. In a preferred embodiment, 5 µl of the enrichment culture is removed and added to 200 µl of lysis solution containing protease. The lysis solution is heated at 37° C. for 20 min followed by protease inactivation at 95° C. for 10 min as described in the BAX® System User's Guide, DuPont Qualicon, Inc., Wilmington, Del.

PCR Assay Methods:

A preferred method for detecting the presence of SEQ ID NOs: 1-3 and subsequently *E. coli* O157:H7 in a sample comprises (a) performing PCR amplification of two or more of SEQ ID NOs: 1-3, preferably all three, using primer pairs listed in Table 1 to produce a PCR amplification result; and (b) detecting the amplification, whereby a positive detection of the amplification indicates the presence of E. coli O157: H7 in the sample.

In another preferred embodiment, prior to performing PCR amplification, a step of preparing the sample may be carried out. The preparing step may comprise at least one of the following processes: (1) bacterial enrichment, (2) separation of bacterial cells from the sample, (3) cell lysis, and (4) total DNA extraction.

Amplification Conditions:

A skilled person will understand that any generally acceptable PCR conditions may be used for successfully detecting SEQ ID NOs: 1-3 and the target E. coli O157:H7 bacteria using the oligonucleotides of the instant invention, and depending on the sample to be tested and other laboratory conditions, routine optimization for the PCR conditions may be necessary to achieve optimal sensitivity and specificity. Optimally, they achieve PCR amplification results from all of the intended specific targets while giving no PCR results for other, non-target species.

Detection/Examination/Analysis:

Primer-directed amplification products of SEQ ID NOs: 1-3 can be analyzed using various methods. Homogenous detection refers to a preferred method for the detection of amplification products where no separation (such as by gel electrophoresis) of amplification products from template or primers is necessary. Homogeneous detection is typically accomplished by measuring the level of fluorescence of the reaction mixture during or immediately following amplification. In addition, heterogeneous detection methods, which involve separation of amplification products during or prior to detection, can be employed in the present invention.

Homogenous detection may be employed to carry out "real-time" primer-directed nucleic acid amplification and detection, using primer pairs of the instant invention (e.g., "real-time" PCR and "real-time" RT-PCR). Preferred "real-time" methods are set forth in U.S. Pat. Nos. 6,171,785, 5,994,056, 6,326,145, 5,804,375, 5,538,848, 5,487,972, and 5,210,015, each of which is hereby incorporated by reference in its entirety.

A particularly preferred "real-time" detection method is the Scorpion probe assay as set forth in U.S. Pat. No. 6,326,145, which is hereby incorporated by reference in its entirety. In the Scorpion probe assay, PCR amplification is performed using a Scorpion probe (either unimolecular or bimolecular) as a primer-probe complex, the Scorpion probe possessing an appropriate reporter-quencher pair to allow the detectable signal of the reporter to be quenched prior to elongation of the primer. Post-elongation, the quenching effect is eliminated and the amount of signal present is quantitated. As the amount of amplification product increases, an equivalent increase in detectable signal will be observed, thus allowing the amount of amplification product present to be determined as a function of the amount of detectable signal measured. When more than one Scorpion probe is employed in a Scorpion probe assay of present invention, such as one directed to each of the three DNA regions of interest (SEQ ID NOs: 1-3), each probe can have a different detectable label (e.g., reporter-quencher pair) attached, thus allowing each probe to be detected independently of the other probes.

In a preferred embodiment of the present invention, amplification and detection of all three of SEQ ID NOs: 1-3 is performed using differentially labeled Scorpion probes. SEQ ID NO:1 is preferably amplified and detected using SEQ ID NO:4 in conjunction with SEQ ID NO:5, with SEQ ID NO:4 possessing a Quasar 670 reporter attached at the 5' terminus and a BHQ2 quencher attached immediately upstream (i.e., in the 5' direction) of the non-amplifiable linker, preferably an 18-carbon linker. SEQ ID NO:2 is preferably amplified and detected using SEQ ID NO:10 in conjunction with SEQ ID NO:11 and SEQ ID NO:12, with SEQ ID NO:10 possessing a 6FAM reporter attached at the 5' terminus and SEQ ID NO:11 possessing a BHQ1 quencher attached at its 3' terminus. SEQ ID NO:3 is preferably amplified and detected using SEQ ID NO:15 in conjunction with SEQ ID NO:16, with SEQ ID NO:15 possessing a Calfluor Orange 560 reporter attached at the 5' terminus and a BHQ1 quencher attached immediately upstream (i.e., in the 5' direction) of the non-amplifiable linker, preferably an 18-carbon linker.

Another preferred "real-time" detection method is the 5'-exonuclease detection method, as set forth in U.S. Pat. Nos. 5,804,375, 5,538,848, 5,487,972, and 5,210,015, each of which is hereby incorporated by reference in its entirety. In the 5'-exonuclease detection assay a modified probe is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are preferably attached to the probe within a few nucleotides of one another, usually within 30 nucleotides of one another, more preferably with a separation of from about 6 to 16 nucleotides. Typically, this separation is achieved by attaching one member of a reporter-quencher pair to the 5' end of the probe and the other member to a nucleotide about 6 to 16 nucleotides away.

Again, when more than one Taqman® probe is employed in a 5'-exonuclease detection assay of present invention, such as one directed to each of the three DNA regions of interest (SEQ ID NOs: 1-3), each probe can have a different detectable label (e.g., reporter-quencher pair) attached, thus allowing each probe to be detected independently of the other probes. Preferred Taqman® probes of the present invention include SEQ ID NOs:24-26, which detect SEQ ID NO:2, SEQ ID NO:1, and SEQ ID NO:3, respectively.

Another preferred method of homogenous detection involves the use of DNA melting curve analysis, particularly with the BAX® System hardware and reagent tablets from DuPont Qualicon Inc. The details of the system are given in U.S. Pat. No. 6,312,930 and PCT Publication Nos. WO 97/11197 and WO 00/66777, each of which is hereby incorporated by reference in its entirety.

Melting curve analysis detects and quantifies double stranded nucleic acid molecule ("dsDNA" or "target") by monitoring the fluorescence of the target amplification product ("target amplicon") during each amplification cycle at selected time points.

As is well known to the skilled artisan, the two strands of a dsDNA separate or melt, when the temperature is higher than its melting temperature. Melting of a dsDNA molecule is a process, and under a given solution condition, melting starts at a temperature (designated $T_{MS}$ hereinafter), and completes at another temperature (designated $T_{ME}$ hereinafter). The familiar term, $T_m$, designates the temperature at which melting is 50% complete.

A typical PCR cycle involves a denaturing phase where the target dsDNA is melted, a primer annealing phase where the temperature optimal for the primers to bind to the now-single-stranded target, and a chain elongation phase (at a temperature $T_E$) where the temperature is optimal for DNA polymerase to function.

According to the present invention, $T_{MS}$ should be higher than $T_E$, and $T_{ME}$ should be lower (often substantially lower) than the temperature at which the DNA polymerase is heat-inactivated. Melting characteristics are effected by the intrinsic properties of a given dsDNA molecule, such as deoxynucleotide composition and the length of the dsDNA.

Intercalating dyes will bind to double stranded DNA. The dye/dsDNA complex will fluoresce when exposed to the appropriate excitation wavelength of light, which is dye dependent, and the intensity of the fluorescence may be proportionate to concentration of the dsDNA. Methods taking advantage of the use of DNA intercalating dyes to detect and quantify dsDNA are known in the art. Many dyes are known and used in the art for these purposes. The instant methods also take advantage of such relationship.

Examples of such intercalating dyes include, but are not limited to, SYBR Green-I®, ethidium bromide, propidium iodide, TOTO®-1 {Quinolinium, 1-1'-[1,3-propanediylbis[(dimethyliminio)-3,1-propanediyl]]bis[4-[(3-methyl-2 (3H)-benzothiazolylidene)methyl]]-, tetraiodide}, and YoPro® {Quinolinium, 4-[(3-methyl-2(3H)-benzoxazolylidene)methyl]-1-[3-(trimethylammonio)-propyl]-, diiodide}. Most preferred for the instant invention is a non-asymmetrical cyanide dye such as SYBR Green-I®, manufactured by Molecular Probes, Inc. (Eugene, Oreg.).

Melting curve analysis is achieved by monitoring the change in fluorescence while the temperature is increased. When the temperature reaches the $T_{MS}$ specific for the target amplicon, the dsDNA begins to denature. When the dsDNA denatures, the intercalating dye dissociates from the DNA and fluorescence decreases. Mathematical analysis of the negative of the change of the log of fluorescence divided by the change in temperature plotted against the temperature results in the graphical peak known as a melting curve.

It should be understood that the present invention could be operated using a combination of these techniques, such as by having a Scorpion probe directed to one target region and a Taqman® probe directed to a second target region. It should also be understood that the invention is not limited to the above described techniques. Rather, one skilled in the art would recognize that other techniques for detecting amplification as known in the art may also be used. For example, techniques such as PCR-based quantitative sequence detection (QSD) may be performed using nucleic acid probes which, when present in the single-stranded state in solution, are configured such that the reporter and quencher are sufficiently close to substantially quench the reporter's emission. However, upon hybridization of the intact reporter-quencher nucleic acid probe with the amplified target nucleic acid sequence, the reporter and quenchers become sufficiently distant from each other. As a result, the quenching is substantially abated causing an increase in the fluorescence emission detected.

In addition to homogeneous detection methods, a variety of other heterogeneous detection methods are known in the art which can be employed in the present invention, including standard non-denaturing gel electrophoresis (e.g., acrylamide or agarose), denaturing gradient gel electrophoresis, and temperature gradient gel electrophoresis. Standard non-denaturing gel electrophoresis is a simple and quick method of PCR detection, but may not be suitable for all applications.

Denaturing Gradient Gel Electrophoresis (DGGE) is a separation method that detects differences in the denaturing behavior of small DNA fragments (200-700 bp). The principle of the separation is based on both fragment length and nucleotide sequence. In fragments that are the same length, a difference as little as one base pair can be detected. This is in contrast to non-denaturing gel electrophoresis, where DNA fragments are separated only by size. This limitation of non-denaturing gel electrophoresis results because the difference in charge density between DNA molecules is near neutral and plays little role in their separation. As the size of the DNA fragment increases, its velocity through the gel decreases.

DGGE is primarily used to separate DNA fragments of the same size based on their denaturing profiles and sequence. Using DGGE, two strands of a DNA molecule separate, or melt, when heat or a chemical denaturant is applied. The denaturation of a DNA duplex is influenced by two factors: 1) the hydrogen bonds formed between complimentary base pairs (since GC rich regions melt at higher denaturing conditions than regions that are AT rich); and 2) the attraction between neighboring bases of the same strand, or "stacking." Consequently, a DNA molecule may have several melting domains with each of their individual characteristic denaturing conditions determined by their nucleotide sequence. DGGE exploits the fact that otherwise identical DNA molecules having the same length and DNA sequence, with the exception of only one nucleotide within a specific denaturing domain, will denature at different temperatures or Tm. Thus, when the double-stranded (ds) DNA fragment is electrophoresed through a gradient of increasing chemical denaturant it begins to denature and undergoes both a conformational and mobility change. The dsDNA fragment will travel faster than a denatured single-stranded (ss) DNA fragment, since the branched structure of the single-stranded moiety of the molecule becomes entangled in the gel matrix. As the denaturing environment increases, the dsDNA fragment will completely dissociate and mobility of the molecule through the gel is retarded at the denaturant concentration at which the particular low denaturing domains of the DNA strand dissociate. In practice, the electrophoresis is conducted at a constant temperature (around 60° C.) and chemical denaturants are used at concentrations that will result in 100% of the DNA molecules being denatured (i.e., 40% formamide and 7M urea). This variable denaturing gradient is created using a gradient maker, such that the composition of each DGGE gel gradually changes from 0% denaturant up to 100% denaturant. Of course, gradients containing a reduced range of denaturant (e.g., 35% to 60%) may also be poured for increased separation of DNA.

The principle used in DGGE can also be applied to a second method that uses a temperature gradient instead of a chemical denaturant gradient. This method is known as Temperature Gradient Gel Electrophoresis (TGGE). This method makes use of a temperature gradient to induce the conformational change of dsDNA to ssDNA to separate fragments of equal size with different sequences. As in DGGE, DNA fragments with different nucleotide sequences will become immobile at different positions in the gel. Variations in primer design can be used to advantage in increasing the usefulness of DGGE for characterization and identification of the PCR products. These methods and principles of using primer design variations are described in PCR Technology Principles and Applications, Henry A. Erlich Ed., M. Stockton Press, NY, pages 71 to 88 (1988).

Instrumentation:

When homogenous detection is employed, the level of fluorescence is preferably measured using a laser fluorometer such as, for example, an ABI Prism Model 7500 Fast Sequence Detector. However, similar detection systems for measuring the level of fluorescence in a sample are included in the invention.

Reagents and Kits:

Any suitable nucleic acid replication composition ("replication composition") in any format can be used. A typical replication composition for PCR amplification may comprise, for example, dATP, dCTP, dGTP, dTTP, target specific primers and a suitable polymerase.

If the replication composition is in liquid form, suitable buffers known in the art may be used (Sambrook, J. et al., supra).

Alternatively, if the replication composition is contained in a tablet form, then typical tabletization reagents may be included such as stabilizers and binding agents. Preferred tabletization technology is set forth in U.S. Pat. Nos. 4,762,857 and 4,678,812, each of which is hereby incorporated by reference in its entirety.

A preferred replication composition of the instant invention comprises (a) at least one primer pair selected from Table 1, and (b) thermostable DNA polymerase. Another preferred replication composition comprises (a) at least two primer pairs selected from Table 1, each directed toward a different target DNA region; and (b) thermostable DNA polymerase. More preferred is inclusion of primer pairs directed to all three of SEQ ID NOs: 1-3.

A more preferred replication composition of the present invention comprises (a) at least two primer pairs and any corresponding probe or blocking oligonucleotide selected from Table 1, wherein each nucleic acid probe or primer-probe complex employed comprises a detectable label; and (b) thermostable DNA polymerase. Preferably the detectable label comprises a reporter capable of emitting a detectable signal and a quencher capable of substantially quenching the reporter and preventing the emission of the detectable signal when the reporter and quencher are in sufficiently close proximity to one another.

A preferred kit of the instant invention comprises any one of the above replication compositions. A preferred tablet of the instant invention comprises any one of the above replication compositions. More preferably, a kit of the instant invention comprises the foregoing preferred tablet.

In some instances, an internal positive control can be included in the reaction. The internal positive control can include control template nucleic acids (e.g. DNA or RNA), control primers, and control nucleic acid probe. The advantages of an internal positive control contained within a PCR reaction have been previously described (U.S. Pat. No. 6,312,930 and PCT Application No. WO 97/11197, each of which is hereby incorporated by reference in its entirety), and include: (i) the control may be amplified using a single primer; (ii) the amount of the control amplification product is independent of any target DNA or RNA contained in the sample; (iii) the control DNA can be tableted with other amplification reagents for ease of use and high degree of reproducibility in both manual and automated test procedures; (iv) the control can be used with homogeneous detection, i.e., without separation of product DNA from reactants; and (v) the internal control has a melting profile that is distinct from other potential amplification products in the reaction and/or a detectable label on the control nucleic acid that is distinct from the detectable label on the nucleic acid probe directed to the target.

Control DNA will be of appropriate size and base composition to permit amplification in a primer-directed amplification reaction. The control template DNA sequence may be obtained from the E. coli genome, or from another source, but must be reproducibly amplified under the same conditions that permit the amplification of the target amplification product.

Preferred control sequences include, for example, control primers SV4219 (SEQ ID NO:21) and SV4313 (SEQ ID NO:22) and probe SV40Probe3 (SEQ ID NO:23) for Taqman® assays and control primers SV40-33-4312 (SEQ ID NO:27) and SV40-29-4222 (SEQ ID NO:28) and control probe SV40 scorpion 1 (SEQ ID NO:29) for Scorpion assays.

The control reaction is useful to validate the amplification reaction. Amplification of the control DNA occurs within the same reaction tube as the sample that is being tested, and therefore indicates a successful amplification reaction when samples are target negative, i.e. no target amplification product is produced. In order to achieve significant validation of the amplification reaction, a suitable number of copies of the control DNA template must be included in each amplification reaction.

In some instances it may be useful to include an additional negative control replication composition. The negative control replication composition will contain the same reagents as the replication composition but without the polymerase. The primary function of such a control is to monitor spurious background fluorescence in a homogeneous format when the method employs a fluorescent means of detection.

Replication compositions may be modified depending on whether they are designed to be used to amplify target DNA or the control DNA. Replication compositions that will amplify the target DNA (test replication compositions) may include (i) a polymerase (generally thermostable), (ii) a primer pair capable of hybridizing to the target DNA and (iii) necessary buffers for the amplification reaction to proceed. Replication compositions that will amplify the control DNA (positive control, or positive replication composition) may include (i) a polymerase (generally thermostable) (ii) the control DNA; (iii) at least one primer capable of hybridizing to the control DNA; and (iv) necessary buffers for the amplification reaction to proceed. In addition, the replication composition for either target DNA or control DNA amplification can contain a nucleic acid probe, preferably possessing a detectable label.

Nucleic Acid Hybridization Methods

In addition to primer-directed amplification assay methods, nucleic acid hybridization assay methods can be employed in the present invention for detection of E. coli O157:H7. The basic components of a nucleic acid hybridization test include a probe, a sample suspected of containing E. coli O157:H7, and a specific hybridization method. Typically the probe length can vary from as few as 5 bases to the full length of the E. coli diagnostic sequence and will depend upon the specific test to be done. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Probes particularly useful in nucleic acid hybridization methods are any of SEQ ID NOs:4-20 or 24-26, or sequences derived therefrom.

The sample may or may not contain *E. coli* O157:H7. The sample may take a variety of forms, however will generally be extracted from an animal, environmental or food source suspected of contamination. The DNA may be detected directly but most preferably, the sample nucleic acid must be made available to contact the probe before any hybridization of probe and target molecule can occur. Thus the organism's DNA is preferably free from the cell and placed under the proper conditions before hybridization can occur. Methods of in-solution hybridization necessitate the purification of the DNA in order to be able to obtain hybridization of the sample DNA with the probe. This has meant that utilization of the in-solution method for detection of target sequences in a sample requires that the nucleic acids of the sample must first be purified to eliminate protein, lipids, and other cell components, and then contacted with the probe under hybridization conditions. Methods for the purification of the sample nucleic acid are common and well known in the art (Sambrook et al., supra).

In one preferred embodiment, hybridization assays may be conducted directly on cell lysates, without the need to extract the nucleic acids. This eliminates several steps from the sample-handling process and speeds up the assay. To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to DNA at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30-50% (v/v).

Alternatively, one can purify the sample nucleic acids prior to probe hybridization. A variety of methods are known to one of skill in the art (e.g., phenol-chloroform extraction, IsoQuick extraction (MicroProbe Corp., Bothell, Wash.), and others). Pre-hybridization purification is particularly useful for standard filter hybridization assays. Furthermore, purification facilitates measures to increase the assay sensitivity by incorporating in vitro RNA amplification methods such as self-sustained sequence replication (see for example Fahy et al., In *PCR Methods and Applications*, Cold Spring Harbor Laboratory: Cold Spring Harbor, N.Y. (1991), pp. 25-33) or reverse transcriptase PCR (Kawasaki, In *PCR Protocols: A Guide to Methods and Applications*, M. A. Innis et al., Eds., (1990), pp. 21-27).

Once the DNA is released, it can be detected by any of a variety of methods. However, the most useful embodiments have at least some characteristics of speed, convenience, sensitivity, and specificity.

Hybridization methods are well known in the art. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed.

Various hybridization solutions can be employed. Typically, these comprise from about 20 to 60% volume, preferably 30%, of a polar organic solvent. A common hybridization solution employs about 30-50% v/v formamide, about 0.15 to 1M sodium chloride, about 0.05 to 0.1M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents which include a variety of polar water-soluble or swellable agents (e.g., polyethylene glycol), anionic polymers (e.g., polyacrylate or polymethylacrylate), and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the DNA sequence.

The sandwich assay may be encompassed in an assay kit. This kit would include a first component for the collection of samples suspected of contamination and buffers for the disbursement and lysis of the sample. A second component would include media in either dry or liquid form for the hybridization of target and probe polynucleotides, as well as for the removal of undesirable and nonduplexed forms by washing. A third component includes a solid support (dipstick) upon which is fixed (or to which is conjugated) unlabeled nucleic acid probe(s) that is (are) complementary to one or more of SEQ ID NOs: 1-3. A fourth component would contain labeled probe that is complementary to a second and different region of the same DNA strand to which the immobilized, unlabeled nucleic acid probe of the third component is hybridized.

In a preferred embodiment, SEQ ID NOs: 4-20 or derivations thereof may be used as 3' blocked detection probes in either a homogeneous or heterogeneous assay format. For example, a probe generated from these sequences may be 3' blocked or non-participatory and will not be extended by, or participate in, a nucleic acid amplification reaction. Additionally, the probe incorporates a label that can serve as a reactive ligand that acts as a point of attachment for the immobilization of the probe/analyte hybrid or as a reporter to produce detectable signal. Accordingly, genomic or cDNA isolated from a sample suspected of *E. coli* contamination is amplified by standard primer-directed amplification protocols in the presence of an excess of the 3' blocked detection probe to produce amplification products. Because the probe is 3' blocked, it does not participate or interfere with the amplification of the target. After the final amplification cycle, the detection probe anneals to the relevant portion of the amplified DNA and the annealed complex is then captured on a support through the reactive ligand.

In some instances it is desirable to incorporate a ligand labeled dNTP, with the label probe in the replication composition to facilitate immobilization of the PCR reaction product on a support and then detection of the immobilized product by means of the labeled probe reagent. For example a biotin, digoxigenin, or digoxin labeled dNTP could be added to PCR reaction composition. The biotin, digoxigenin, or digoxin incorporated in the PCR product could then be immobilized respectively on to a strepavidin, antidigoxigenin or antidigoxigenin antibody support. The immobilized PCR product could then be detected by the presence of the probe label.

EXAMPLES

The present invention is further defined in the following Examples. It should be understood that these Examples, while indicating preferred embodiments of the invention, are given by way of illustration only.

General Methods and Materials Used in the Examples

Materials and methods suitable for the maintenance and growth of bacterial cultures are well known in the art. Techniques suitable for use in the following Examples may be found in Manual of Methods for Genus Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in Biotechnology: A Textbook of Industrial Microbiology, Second Edition (1989) Sinauer Associates, Inc., Sunderland, Mass. or Bacteriological Analytical Manual. 6th Edition, Association of Official Analytical Chemists, Arlington, Va. (1984).

The medium used to grow the pathogenic *E. coli* strains and comparative non-target strains was Brain Heart Infusion broth (BHI) obtained from BBL (Becton-Dickenson).

Samples of pathogenic *E. coli* strains were obtained from cultures grown overnight in BHI broth then diluted to approximately $10^6$ cfu/ml in 0.1% peptone water. Samples of the comparative non-target strains were enriched in BHI at approximately $10^9$ cfu/ml.

Primers and probes (SEQ ID NOs: 4-29) were prepared by Sigma-Genosys, Woodlands, Tex.

All PCR reactions were carried out using a standard BAX® System (DuPont Qualicon, Wilmington, Del.).

The meaning of abbreviations is as follows: "h" means hour(s), "min" means minute(s), "sec" means second(s), "d" means day(s), "ml" means milliliter(s), "µl" means microliter(s), "cfu" means colony forming unit(s).

Example 1

Determination of Inclusivity/Exclusivity of the Individual Targets Via Taqman® Assay Samples of organisms were analyzed to establish inclusivity and exclusivity of individual Taqman® probes of the present invention. Pure cultures grown overnight achieved cell densities of $8 \times 10^8$ to $2 \times 10^9$ cfu/ml. For inclusivity, independent, bona fide *E. coli* O157:H7 isolates were used; for exclusivity non O157:H7 *E. coli* were used to ensure that the assay would discriminate the target organism (O157:H7) from other *E. coli*.

DNA Lysate Preparation

Material tested was either food enrichment (ground beef enrichment prepared as described in the BAX® system user guide for the BAX® MP assay) or overnight growth of *E. coli* O157:H7 isolates at 37° C. in BHI media. 20 µl of the material to be tested was added to 200 µl of BAX® lysis reagent (DuPont Qualicon, Wilmington, Del.). The mixture was incubated at 37° C. for 20 minutes, then further incubated at 95° C. for 10 minutes, and finally cooled to 5° C.

PCR Conditions

30 µl of the DNA lysate as prepared above was used to hydrate lyophylized PCR reaction components to achieve a DNA lysate/PCR reaction component mixture containing the primers and probes listed in TABLE 2.

TABLE 2

| Primers | Per reaction | | |
|---|---|---|---|
| wbdRa1F (SEQ ID NO: 17) | 15 pMole | | |
| wbdra2R (SEQ ID NO: 16) | 15 pMole | | |
| PerSt73F (SEQ ID NO: 13) | 12 pMole | | |
| PerSt73R (SEQ ID NO: 12) | 12 pMole | | |
| SIS1T74F (SEQ ID NO: 6) | 12 pMole | | |
| SIS1T75R (SEQ ID NO: 5) | 12 pMole | | |
| SV4219 (SEQ ID NO: 21) | 20 pMole | | |
| SV4313 (SEQ ID NO: 22) | 20 pMole | | |
| Probes | Per reaction | 5' Fluor | Quencher |
| SV40Probe3 (SEQ ID NO: 23) | 10 pMole | Calflour Orange 560 | BHQ1 |
| Perstalt166p (SEQ ID NO: 24) | 5 pMole | Quasar 670 | BHQ1 |
| SIS1T65P (SEQ ID NO: 25) | 10 pMole | FAM | BHQ1 |
| wbdRa1P (SEQ ID NO: 26) | 12.5 pMole | Tamra | BHQ1 |

This DNA lysate/PCR reaction component mixture was added to a PCR reaction mixture. The reagents that were used in the PCR amplification reaction were from BAX® System Reagent Tablet Kits (DuPont Qualicon, Wilmington, Del.) and include SYBR® Green (Molecular Probes, Eugene, Oreg.), Taq DNA Polymerase (Applied Biosystems, Foster City, Calif.), deoxynucleotides (Roche Diagnostics, Indianapolis, Ind.), and buffer (EM Science, New Jersey).

Amplification and testing was performed on the BAX® Q7 machine (DuPont Qualicon, Wilmington, Del.). The thermal cycling conditions were: 2 minutes at 94° C., followed by 40 cycles of 94° C. for 10 seconds and 60° C. for 30 seconds, with the fluorescent signal captured during the 60° C. step at each cycle.

Results

As can be seen in Table 3, below, using individual Taqman® probes, the method of the present invention was able to almost completely distinguish between O157:H7 and non-O157:H7 E. coli strains.

TABLE 3

Inclusivity Panel: 36 E. coli O157:H7 isolates

| Sample ID | Taqman ® Version SIS1 Target 1 Result | Perosamine Synthetase Target 2 Result | wbdr Target 3 Result |
|---|---|---|---|
| DD935 | Positive | Positive | Positive |
| DD1449 | Positive | Positive | Positive |
| DD1450 | Positive | Positive | Positive |
| DD1451 | Positive | Positive | Positive |
| DD1452 | Positive | Positive | Positive |
| DD1453 | Positive | Positive | Positive |
| DD1454 | Positive | Positive | Positive |
| DD1455 | Positive | Positive | Positive |
| DD1456 | Positive | Positive | Positive |
| DD1457 | Positive | Positive | Positive |
| DD1458 | Positive | Positive | Positive |
| DD1459 | Positive | Positive | Positive |
| DD1460 | Positive | Positive | Positive |
| DD1461 | Positive | Positive | Positive |
| DD1462 | Positive | Positive | Positive |
| DD1463 | Positive | Positive | Positive |
| DD1972 | Positive | Positive | Positive |
| DD1973 | Positive | Positive | Positive |
| DD1974 | Positive | Positive | Positive |
| DD1975 | Positive | Positive | Positive |
| DD1976 | Positive | Positive | Positive |
| DD1977 | Positive | Positive | Positive |
| DD1978 | Positive | Positive | Positive |
| DD1979 | Positive | Positive | Positive |
| DD1980 | Positive | Positive | Positive |
| DD1981 | Positive | Positive | Positive |
| DD1982 | Positive | Positive | Positive |
| DD1983 | Positive | Positive | Positive |
| DD1984 | Positive | Positive | Positive |
| DD1985 | Positive | Positive | Positive |
| DD1986 | Positive | Positive | Positive |
| DD1987 | Positive | Positive | Positive |
| DD1988 | Positive | Positive | Positive |
| DD1989 | Positive | Positive | Positive |
| DD1990 | Positive | Positive | Positive |
| DD1991 | Positive | Positive | Positive |

TABLE 4

Exclusivity Panel: 45 E. coli non-O157:H7 isolates

| Sample ID | Taqman ® Version SIS1 Target 1 Result | Perosamine Synthetase Target 2 Result | wbdr Target 3 Result |
|---|---|---|---|
| DD1797 | Negative | — | — |
| DD1808 | Negative | Negative | Negative |
| DD1809 | Negative | Negative | Negative |
| DD1821 | Negative | Negative | Negative |
| DD1845 | Negative | Negative | Negative |
| DD1858 | Negative | Negative | Negative |
| DD1859 | Negative | Negative | Negative |
| DD1869 | Negative | Negative | Negative |
| DD1870 | Negative | Negative | Negative |
| DD1906 | Negative | Negative | Negative |
| DD1915 | Negative | Negative | Negative |
| DD1927 | Negative | Negative | Negative |
| DD1931 | Negative | Negative | Negative |
| DD2448 | Negative | Negative | Negative |
| DD2450 | Negative | Negative | Negative |
| DD2453 | Negative | Negative | Negative |
| DD2474 | Negative | Negative | Negative |
| DD2508 | Negative | Negative | Negative |
| DD2511 | Negative | Negative | Negative |
| DD2514 | Negative | Negative | Negative |
| DD2517 | Negative | Negative | Negative |
| DD2518 | Negative | Negative | Negative |
| DD2522 | Negative | Negative | Negative |
| DD2523 | Negative | Negative | Negative |
| DD3124 | Negative | Negative | Negative |
| DD3127 | Negative | Negative | Negative |
| DD3130 | Negative | Negative | Negative |
| DD3132 | Negative | Negative | Negative |
| DD3166 | Negative | Negative | Negative |
| DD3197 | Negative | Negative | Negative |
| DD3199 | Negative | Negative | Negative |
| DD3204 | Negative | Negative | Negative |
| DD3208 | Negative | Negative | Negative |
| DD3210 | Negative | Negative | Negative |
| DD3785 | Negative | Negative | Negative |
| DD5884 | Negative | Negative | Negative |
| DD5887 | Negative | Negative | Negative |
| DD5901 | Negative | Negative | Negative |
| DD9705 | Negative | Negative | Negative |
| DD10910 | Positive | Negative | Negative |
| DD12901 | Negative | Negative | Negative |
| DD5883 | Negative | Negative | Negative |
| DD12800 | Negative | Negative | Negative |
| DD12804 | Negative | Negative | Negative |
| DD12849 | Negative | Negative | Negative |
| DD12851 | Negative | Negative | Negative |

Example 2

Determination of Inclusivity/Exclusivity of the Individual Targets Via Scorpion Assay Samples of organisms were analyzed to establish inclusivity and exclusivity of individual Scorpion probes of the present invention. Pure cultures grown overnight achieved cell densities of $8 \times 10^8$ to $2 \times 10^9$ cfu/ml. For inclusivity, independent, bona fide E. coli O157:H7 isolates were used; for exclusivity non O157:H7 E. coli were used to ensure that the assay would discriminate the target organism (O157:H7) from other E. coli.

DNA Lysate Preparation

Material tested was either food enrichment (ground beef enrichment prepared as described in the BAX® system user guide for the BAX® MP assay) or overnight growth of E. coli O157:H7 isolates at 37° C. in BHI media. 20 µl of the material to be tested was added to 200 µl of BAX® lysis reagent (DuPont Qualicon, Wilmington, Del.). The mixture was incubated at 37° C. for 20 minutes, then further incubated at 95° C. for 10 minutes, and finally cooled to 5° C.

PCR Conditions

30 µl of the DNA lysate as prepared above was used to hydrate lyophilized PCR reaction components to achieve a DNA lysate/PCR reaction component mixture containing the primers and probes listed in TABLE 5.

TABLE 5

| Primers | Per reaction | | |
|---|---|---|---|
| wbdra2R (SEQ ID NO: 16) | 20 pMole | | |
| PerSt73R (SEQ ID NO: 12) | 20 pMole | | |
| SIS1T75R (SEQ ID NO: 5) | 20 pMole | | |
| SV40-33-4312 (SEQ ID NO: 27) | 20 pMole | | |
| SV40-29-4222 (SEQ ID NO: 28) | 2.5 pMole | | |
| Probes | Per reaction | 5' Fluor | Quencher |
| WBDR scorpion 1 (SEQ ID NO: 15) | 15 pMole | Calflour Orange 560 | BHQ1 |
| SIS1 scorpion 1 (SEQ ID NO: 4) | 5 pMole | Quasar 670 | BHQ2 |
| SV40 scorpion 1 (SEQ ID NO: 29) | 10 pMole | Tamra | BHQ2 |
| PERSYNA probe 1 (SEQ ID NO: 10) | 20 pMole | 6FAM | n/a |
| PERSYNA probe 2 (SEQ ID NO: 11) | 200 pMole | n/a | BHQ1 | n/a = not applicable

SEQ ID NO:15 (WBDR scorpion 1 probe) is presented in the sequence listing as the entire sequence without modifications. For this Example, the WBDR scorpion probe has, following nucleotide number 45 in SEQ ID NO:15, an internal BHQ1 quencher and an SP-18 blocker followed by the remaining 42 nucleotides. Similarly, SEQ ID NO:4 (SIS1 scorpion 1 probe) is presented in the sequence listing as the entire sequence without modifications. For this Example, the SIS1 scorpion probe has, following nucleotide number 46 in SEQ ID NO:4, an internal BHQ2 quencher and an SP-18 blocker followed by the remaining 40 nucleotides. Also, SEQ ID NO:29 (SV40 scorpion 1 probe) is presented in the sequence listing as the entire sequence without modifications. For this Example, the SV40 scorpion probe has, following nucleotide number 52 in SEQ ID NO:29, an internal BHQ2 quencher and an SP-18 blocker followed by the remaining 26 nucleotides.

The DNA lysate/PCR reaction component mixture was added to a PCR reaction mixture. The reagents that were used in the PCR amplification reaction were from BAX® System Reagent Tablet Kits (DuPont Qualicon, Wilmington, Del.) and include SYBR® Green (Molecular Probes, Eugene, Oreg.), Taq DNA Polymerase (Applied Biosystems, Foster City, Calif.), deoxynucleotides (Roche Diagnostics, Indianapolis, Ind.), and buffer (EM Science, New Jersey).

Amplification and testing was performed on the BAX® Q7 machine (DuPont Qualicon, Wilmington, Del.). The thermal cycling conditions were: 2 minutes at 94° C., followed by 40 cycles of 94° C. for 10 seconds and 63° C. for 40 seconds, with the fluorescent signal captured during the 63° C. step at each cycle.

Results

As can be seen in Table 6, below, using individual Scorpion probes, the method of the present invention was able to almost completely distinguish between O157:H7 and non-O157:H7 E. coli strains.

TABLE 6

Inclusivity Panel: 36 E. coli O157:H7 isolates

| Sample ID | Scorpion Version SIS1 Target 1 Result | Perosamine Synthetase Target 2 Result | wbdr Target 3 Result |
|---|---|---|---|
| DD935 | Positive | Positive | Positive |
| DD1449 | Positive | Positive | Positive |
| DD1450 | Positive | Positive | Positive |
| DD1451 | Positive | Positive | Positive |
| DD1452 | Positive | Positive | Positive |
| DD1453 | Positive | Positive | Positive |
| DD1454 | Positive | Positive | Positive |
| DD1455 | Positive | Positive | Positive |
| DD1456 | Positive | Positive | Positive |
| DD1457 | Positive | Positive | Positive |
| DD1458 | Positive | Positive | Positive |
| DD1459 | Positive | Positive | Positive |
| DD1460 | Positive | Positive | Positive |
| DD1461 | Positive | Positive | Positive |
| DD1462 | Positive | Positive | Positive |
| DD1463 | Positive | Positive | Positive |
| DD1972 | Positive | Positive | Positive |
| DD1973 | Positive | Positive | Positive |
| DD1974 | Positive | Positive | Positive |
| DD1975 | Positive | Positive | Positive |
| DD1976 | Positive | Positive | Positive |
| DD1977 | Positive | Positive | Positive |
| DD1978 | Positive | Positive | Positive |
| DD1979 | Positive | Positive | Positive |
| DD1980 | Positive | Positive | Positive |
| DD1981 | Positive | Positive | Positive |
| DD1982 | Positive | Positive | Positive |
| DD1983 | Positive | Positive | Positive |
| DD1984 | Positive | Positive | Positive |
| DD1985 | Positive | Positive | Positive |
| DD1986 | Positive | Positive | Positive |
| DD1987 | Positive | Positive | Positive |
| DD1988 | Positive | Positive | Positive |
| DD1989 | Positive | Positive | Positive |
| DD1990 | Positive | Positive | Positive |
| DD1991 | Positive | Positive | Positive |

TABLE 7

Exclusivity Panel: 45 *E. coli* non-O157:H7 isolates

| Sample ID | Scorpion Version SIS1 Target 1 Result | Perosamine Synthetase Target 2 Result | wbdr Target 3 Result |
|---|---|---|---|
| DD1797 | Negative | — | — |
| DD1808 | Negative | Negative | Negative |
| DD1809 | Negative | Negative | Negative |
| DD1821 | Negative | Negative | Negative |
| DD1845 | Negative | Negative | Negative |
| DD1858 | Negative | Negative | Negative |
| DD1859 | Negative | Negative | Negative |
| DD1869 | Negative | Negative | Negative |
| DD1870 | Negative | Negative | Negative |
| DD1906 | Negative | Negative | Negative |
| DD1915 | Negative | Negative | Negative |
| DD1927 | Negative | Negative | Negative |
| DD1931 | Negative | Negative | Negative |
| DD2448 | Negative | Negative | Negative |
| DD2450 | Negative | Negative | Negative |
| DD2453 | Negative | Negative | Negative |
| DD2474 | Negative | Negative | Negative |
| DD2508 | Negative | Negative | Negative |
| DD2511 | Negative | Negative | Negative |
| DD2514 | Negative | Negative | Negative |
| DD2517 | Negative | Negative | Negative |
| DD2518 | Negative | Negative | Negative |
| DD2522 | Negative | Negative | Negative |
| DD2523 | Negative | Negative | Negative |
| DD3124 | Negative | Negative | Negative |
| DD3127 | Negative | Negative | Negative |
| DD3130 | Negative | Negative | Negative |
| DD3132 | Negative | Negative | Negative |
| DD3166 | Negative | Negative | Negative |
| DD3197 | Negative | Negative | Negative |
| DD3199 | Negative | Negative | Negative |
| DD3204 | Negative | Negative | Negative |
| DD3208 | Negative | Negative | Negative |
| DD3210 | Negative | Negative | Negative |
| DD3785 | Negative | Negative | Negative |
| DD5884 | Negative | Negative | Negative |
| DD5887 | Negative | Negative | Negative |
| DD5901 | Negative | Negative | Negative |
| DD9705 | Negative | Negative | Negative |
| DD10910 | Positive | Negative | Negative |
| DD12901 | Negative | Negative | Negative |
| DD5883 | Negative | Negative | Negative |
| DD12800 | Negative | Negative | Negative |
| DD12804 | Negative | Negative | Negative |
| DD12849 | Negative | Negative | Negative |
| DD12851 | Negative | Negative | Negative |

Example 3

Determination of Inclusivity/Exclusivity of a Combination of SIS1 and Wbdr Targets Via Scorpion Assay Samples of organisms were analyzed to establish inclusivity and exclusivity of a combination of multiple Scorpion probes of the present invention. For inclusivity, independent, bona fide *E. coli* O157:H7 isolates were used; for exclusivity non O157:H7 *E. coli* were used to ensure that the assay would discriminate the target organism (O157:H7) from other *E. coli*. Inclusivity and exclusivity testing was performed on the BAX® Q7 machine as described above.

Test Panel

The inclusivity panel was largely obtained from the Pennsylvania State University Department of Veterinary Science *E. coli* Reference Center and the DuPont Qualicon culture collection. Isolates originated from a wide range of diagnostic and non-diagnostic samples. Inclusivity strains (n=61) included five strains of O157:H-non motile that were genetically O157:H7, one of the minor genetic clade "cluster A", and one of an O-rough phenotype that is genetically O157:H7. The exclusivity panel of non-*E. coli*, *E. coli* non-O157:H7, and *E. coli* O157 non-H7 strains (n=72) were chosen from the DuPont Qualicon culture collection. Most of these isolates were originally obtained from naturally contaminated food samples or from animal sources, and all identifications were confirmed bio-chemically and/or serologically, as appropriate.

DNA Lysate Preparation

Cultures were struck for purity on BHI agar. For each strain, one colony was inoculated into a tube containing BHI broth (exclusivity testing) or test broth enrichment (inclusivity testing). Cultures were incubated overnight at 35° C. to reach cell densities of approximately $10^9$ bacterial cells per mL. For exclusivity testing, cultures were tested with no dilution. For inclusivity testing, cultures were diluted to $10^5$ cfu/mL, which is ~1 log over the claimed sensitivity of the assay. 20 µl of the material to be tested was added to 200 µl of BAX® lysis reagent (DuPont Qualicon, Wilmington, Del.). The mixture was incubated at 37° C. for 20 minutes, then further incubated at 95° C. for 10 minutes, and finally cooled to 5° C.

PCR Conditions

30 µl of the DNA lysate as prepared above was used to hydrate lyophilized PCR reaction components to achieve a DNA lysate/PCR reaction component mixture containing the primers and probes listed in Table 8.

TABLE 8

| Primers | Per reaction | | |
|---|---|---|---|
| wbdra2R (SEQ ID NO: 16) | 20 pMole | | |
| SIS1T75R (SEQ ID NO: 5) | 20 pMole | | |
| SV40-33-4312 (SEQ ID NO: 27) | 20 pMole | | |
| SV40-29-4222 (SEQ ID NO: 28) | 2.5 pMole | | |
| Probes | Per reaction | 5' Fluor | Quencher |
| WBDR scorpion 1 (SEQ ID NO: 15) | 15 pMole | Calflour Orange 560 | BHQ1 |
| SIS1 scorpion 1 (SEQ ID NO: 4) | 5 pMole | Quasar 670 | BHQ2 |
| SV40 scorpion 1 (SEQ ID NO: 29) | 5 pMole | TAMRA | BHQ2 |

SEQ ID NO:15 (WBDR scorpion 1 probe) is presented in the sequence listing as the entire sequence without modifications. For this Example, the WBDR scorpion probe has, following nucleotide number 45 in SEQ ID NO:15, an internal BHQ1 quencher and an SP-18 blocker followed by the remaining 42 nucleotides. Similarly, SEQ ID NO:4 (SIS1 scorpion 1 probe) is presented in the sequence listing as the entire sequence without modifications. For this Example, the SIS1 scorpion probe has, following nucleotide number 46 in SEQ ID NO:4, an internal BHQ2 quencher and an SP-18 blocker followed by the remaining 40 nucleotides. Also, SEQ ID NO:29 (SV40 scorpion 1 probe) is presented in the sequence listing as the entire sequence without modifications. For this Example, the SV40 scorpion probe has, following nucleotide number 52 in SEQ ID NO:29, an internal BHQ2 quencher and an SP-18 blocker followed by the remaining 26 nucleotides.

The DNA lysate/PCR reaction component mixture was added to a PCR reaction mixture comprising typical PCR ingredients including nucleotides, Taq polymerase and reaction buffer to perform PCR.

Amplification and testing was performed on the BAX® Q7 machine (DuPont Qualicon, Wilmington, Del.). The thermal cycling conditions were: 2 minutes at 94° C., followed by 40 cycles of 94° C. for 10 seconds and 63° C. for 40 seconds, with the fluorescent signal captured during the 63° C. step at each cycle.

Results

As shown in Tables 9 and 10, below, all isolates of *E. coli* O157:H7 gave positive results, while all non-*E. coli* and *E. coli* which were not O157:H7 tested negative.

TABLE 9

Inclusivity panel: 61 *E. coli* O157:H7 isolates

| Strain Number | Strain | Source | Assay Result | Strain Number | Strain | Source | Assay Result |
|---|---|---|---|---|---|---|---|
| 12836 | *E. coli* O157:H7 | PSU Reference Lab | POS | 12848 | *E. coli* O157:H7 | PSU Reference Lab | POS |
| 12830 | *E. coli* O157:H7 | PSU Reference Lab | POS | 12859 | *E. coli* O157:H7 | PSU Reference Lab | POS |
| 12832 | *E. coli* O157:H7 | PSU Reference Lab | POS | 12860 | *E. coli* O157:H7 | PSU Reference Lab | POS |
| 12833 | *E. coli* O157:H7 | PSU Reference Lab | POS | 12861 | *E. coli* O157:H7 | PSU Reference Lab | POS |
| 12844 | *E. coli* O157:H7 | PSU Reference Lab | POS | 12862 | *E. coli* O157:H7 | PSU Reference Lab | POS |
| 12845 | *E. coli* O157:H7 | PSU Reference Lab | POS | 12863 | *E. coli* O157:H7 | PSU Reference Lab | POS |
| 12846 | *E. coli* O157:H7 | PSU Reference Lab | POS | 12874 | *E. coli* O157:H7 | PSU Reference Lab | POS |
| 12835 | *E. coli* O157:H7 | PSU Reference Lab | POS | 12875 | *E. coli* O157:H7 | PSU Reference Lab | POS |
| 12834 | *E. coli* O157:H7 | PSU Reference Lab | POS | 12876 | *E. coli* O157:H7 | PSU Reference Lab | POS |
| 12839 | *E. coli* O157:H7 | PSU Reference Lab | POS | 12857 | *E. coli* O157:H7 | PSU Reference Lab | POS |
| 12840 | *E. coli* O157:H7 | PSU Reference Lab | POS | 12858 | *E. coli* O157:H7 | PSU Reference Lab | POS |
| 12841 | *E. coli* O157:H7 | PSU Reference Lab | POS | 12869 | *E. coli* O157:H7 | PSU Reference Lab | POS |
| 12842 | *E. coli* O157:H7 | PSU Reference Lab | POS | 12870 | *E. coli* O157:H7 | PSU Reference Lab | POS |
| 12843 | *E. coli* O157:H7 | PSU Reference Lab | POS | 12871 | *E. coli* O157:H7 | PSU Reference Lab | POS |
| 12854 | *E. coli* O157:H7 | PSU Reference Lab | POS | 12873 | *E. coli* O157:H7 | PSU Reference Lab | POS |
| 12855 | *E. coli* O157:H7 | PSU Reference Lab | POS | 12884 | *E. coli* O157:H7 | PSU Reference Lab | POS |
| 12856 | *E. coli* O157:H7 | PSU Reference Lab | POS | 12885 | *E. coli* O157:H7 | PSU Reference Lab | POS |
| 12837 | *E. coli* O157:H7 | PSU Reference Lab | POS | 12887 | *E. coli* O157:H7 | PSU Reference Lab | POS |
| 12849 | *E. coli* O157:H7 | PSU Reference Lab | POS | 12867 | *E. coli* O157:H7 | PSU Reference Lab | POS |
| 12850 | *E. coli* O157:H7 | PSU Reference Lab | POS | 12868 | *E. coli* O157:H7 | PSU Reference Lab | POS |
| 12851 | *E. coli* O157:H7 | PSU Reference Lab | POS | 12879 | *E. coli* O157:H7 | PSU Reference Lab | POS |
| 12852 | *E. coli* O157:H7 | PSU Reference Lab | POS | 12880 | *E. coli* O157:H7 | PSU Reference Lab | POS |
| 12853 | *E. coli* O157:H7 | PSU Reference Lab | POS | 12881 | *E. coli* O157:H7 | PSU Reference Lab | POS |
| 12864 | *E. coli* O157:H7 | PSU Reference Lab | POS | 12882 | *E. coli* O157:H7 | PSU Reference Lab | POS |
| 12865 | *E. coli* O157:H7 | PSU Reference Lab | POS | 12883 | *E. coli* O157:H7 | PSU Reference Lab | POS |
| 12847 | *E. coli* O157:H7 | PSU Reference Lab | POS | 12810 | *E. coli* O157:H7 | PSU Reference Lab | POS |
| 12813 | *E. coli* O157:H7 | PSU Reference Lab | POS | 12816 | *E. coli* O157:H7 | PSU Reference Lab | POS |

TABLE 9-continued

Inclusivity panel: 61 E. coli O157:H7 isolates

| Strain Number | Strain | Source | Assay Result | Strain Number | Strain | Source | Assay Result |
|---|---|---|---|---|---|---|---|
| 2485 | E. coli O157:HNM | Unknown | POS | 8301 | E. coli O157:HNM | Unknown | POS |
| 5893 | E. coli O157:HNM | Unknown | POS | 8302 | E. coli O157:HNM | Unknown | POS |
| 5894 | E. coli O157:HNM | Unknown | POS | TD8136 | E. coli O157:H7 Cluster A | Bovine | POS |
| MA06 | E. coli O157:H7 rough | Peter Feng, FDA | POS | | | | |

TABLE 10

Exclusivity panel: 72 non-E. coli or E. coli non-O157:H7 isolates

| Strain Number | Strain | Source | Assay Result | Strain Number | Strain | Source | Assay Result |
|---|---|---|---|---|---|---|---|
| DD1081 | Shigella boydii | Unknown | NEG | DD2434 | E. coli O1:H7 | Unknown | NEG |
| DD11348 | Enterobacter | Unknown | NEG | DD2443 | E. coli O157:H19 | Unknown | NEG |
| DD1152 | Listeria | Pate' | NEG | DD2491 | E. coli O2:H7 | Unknown | NEG |
| DD1261 | Salmonella | Duck | NEG | DD2520 | E. coli O113:H7 | Unknown | NEG |
| DD13249 | Vibrio | raw | NEG | DD2614 | Edwardsiella | Human feces | NEG |
| DD1716 | E. coli O158:H23 | Unknown | NEG | DD2901 | Bacillus cereus | Cream cake | NEG |
| DD1718 | E. coli O128:H2 | Unknown | NEG | DD2992 | Salmonella | Unknown | NEG |
| DD1719 | E. coli O28:HNM | Unknown | NEG | DD3017 | Salmonella | Unknown | NEG |
| DD1720 | E. coli O26:HNM | Unknown | NEG | DD3019 | Salmonella | Unknnown | NEG |
| DD1721 | E. coli O114:H32 | Unknown | NEG | DD3064 | Morganella | Environmental | NEG |
| DD1722 | E. coli O127:HNM | Unknown | NEG | DD3981 | Enterococcus | urine | NEG |
| DD1723 | E. coli O119:H27 | Unknown | NEG | DD3982 | Pseudomonas | Blood culture | NEG |
| DD1724 | E. coli O18:H14 | Unknown | NEG | DD3998 | Streptococcus | Bovine mastitis | NEG |
| DD1725 | E. coli O125:H19 | Unknown | NEG | DD4160 | Staphylococcus | Howler monkey | NEG |
| DD1777 | Salmonella | Unknown | NEG | DD5588 | Hafnia alvei | Ground beef | NEG |
| DD1810 | E. coli O28:H16 | Unknown | NEG | DD577 | Pseudomonas | Human | NEG |
| DD1811 | E. coli O127:H40 | Unknown | NEG | DD5883 | E. coli O55:H10 | Unknown | NEG |
| DD1812 | E. coli O127:H10 | Unknown | NEG | DD610 | Staphylococcus | ham | NEG |
| DD1814 | E. coli O6:H- | Unknown | NEG | DD6121 | Proteus mirabilis | Gull, cloacal | NEG |
| DD1817 | E. coli O29:H- | Unknown | NEG | DD649 | Listeria ivanovii | sheep | NEG |
| DD1818 | E. coli O136:H8 | Unknown | NEG | DD6523 | Klebsiella | Ground beef | NEG |
| DD1819 | E. coli O18:HNM | Unknown | NEG | DD655 | E. coli O101:K- | Calf Intestine | NEG |
| DD1820 | E. coli O86:H8 | Unknown | NEG | DD661 | Pseudomonas | pre-filter tanks | NEG |
| DD1821 | E. coli O55:H- | Unknown | NEG | DD6719 | Escherichia | Sesame seeds | NEG |
| DD1822 | E. coli O28:H8, 4, 3 | Unknown | NEG | DD6832 | Shigella sonnei | Unknown | NEG |
| DD1824 | E. coli O125:HNM | Unknown | NEG | DD687 | Lactobacillus | vacuum | NEG |
| DD1825 | E. coli O25:H8 | Unknown | NEG | DD7005 | Salmonella | Unknown | NEG |
| DD1827 | E. coli O20:HNM | Unknown | NEG | DD7344 | Lactobacillus | Human | NEG |
| DD1831 | E. coli O26:H11 | Unknown | NEG | DD846 | Escherichia | Cockroach | NEG |
| DD1833 | E. coli O55:H9 | Unknown | NEG | DD847 | Escherichia | Human feces | NEG |
| DD1834 | E. coli O29:H51 | Unknown | NEG | DD849 | Escherichia | Unknown | NEG |
| DD1835 | E. coli O127:H- | Unknown | NEG | DD850 | Escherichia | Human wound | NEG |
| DD1908 | E. coli O25:H7 | Unknown | NEG | DD922 | Listeria innocua | cured ham | NEG |
| DD2166 | Salmonella | Unknown | NEG | TD2631 | Vibrio fluvialis | Unknown | NEG |
| DD2274 | Salmonella | Unknown | NEG | TD3122 | Vibrio vulnificus | Unknown | NEG |
| DD2341 | Salmonella | Unknown | NEG | TD3136 | Vibrio cholera | Unknown | NEG |

Example 4

Comparative Sensitivity of Present Detection Methods Vs. USDA Standard Method in Beef Trim Sample This study was performed to validate the ability of the present O157:H7 detection test and methods to consistently detect 1-3 CFU of E. coli O157:H7 in a 375 gram sample of beef trim using a 1:5 sample to media ratio.

Materials and Methods:

In each of three assay runs, twenty five 375 g beef trim samples were spiked at a target of 1.5 CFU per 375 g sample with E. coli O157:H7 (strain DD1450 from DuPont collection). An unspiked media control was run as well on each run. Each run was performed on a different day. Spiking was performed using a single isolate of E. coli O157:H7 that exhibits the phenotypes more commonly seen in E. coli O157:H7 (tellurite resistant, sorbitol non-fermenting, and sufficient expression of the O antigen to render it routinely detectable by IMS prior to plating) in order to simplify the confirmation process (plating on CT-SMAC) as described by the United States Department of Agriculture's Microbiology Laboratory Guidebook (USDAMLG).

A single colony for the strain to be used was picked from a streak plate, used to inoculate 10 mL of Brain Heart Infusion (BHI) medium, and incubated at 37° C. for 24±2 h. This overnight growth was stored at 5° C. until use (24 to 48 hours) while serial dilutions were performed in peptone water and the number of colony forming units determined by plating dilutions on BHI agar plates incubated at 37° C. for 24±2 h. Plates from dilutions with between 30 and 300 colonies were used for CFU per mL determination of the culture. Cultures were then serially diluted to generate a target inoculum of 1.5 CFU/per inoculum volume with an inoculum volume between 10 and 1000 μL. Spike levels were confirmed at time of inoculation by triplicate plating of the sample inoculum volume for each culture used on to BHI agar plates followed by incubation at 37° C. for 18-24 hours and counting of colonies.

375 gram aliquots of trim cut as for n=60 surface sample analysis were held at 2-8° C. for 12-14 hours prior to inoculation. In addition, cultures were held at 2-8° C. for 24 hours prior to being used to spike beef samples. Following spiking, bacteria were further cold stressed on the meat for 18-24 hrs at 2-8° C. before start of enrichment. Spiked beef samples were removed from refrigeration and held at room temperature for no more than 5 minutes prior to addition of 1.5 liters of BAX® MP media pre-warmed to 45±2° C. Following addition of media, samples were hand massaged to disperse trim fragments and the cultures moved to an incubator held at 42±2° C. Samples were removed at times indicated for testing.

At nine hours of incubation, samples were removed for testing. Lysates of the enrichment broth were prepared and tested using both the new assay, as described below, and the standard United States Department of Agriculture Microbiology Laboratory Guidebook (USDAMLG) PCR method (BAX® MP method).

Cells were grown overnight in BHI media. The cell lysate was prepared as for the BAX® system *E. coli* multiplex (MP) test (as described in the BAX® user's guide, E.I. du Pont de Nemours & Co., Wilmington, Del.). Lysates were then used to hydrate tablets containing thermostable polymerase, dNTPs, buffers, and salts and excipients suitable for carrying out PCR. The reagents specific for detection of the targets in this patent as well as the cycle conditions are described below in Tables 11 (Taqman® assay) and 12 (Scorpion assay).

TABLE 11

| Primers | Per 30 μl reaction | Concentration in Reaction | 5' Fluor | Quencher |
|---|---|---|---|---|
| wbdRa1F (SEQ ID NO: 17) | 15 pMole | 0.5 μM | | |
| wbdra2R (SEQ ID NO: 16) | 15 pMole | 0.5 μM | | |
| PerSt73F (SEQ ID NO: 13) | 12 pMole | 0.4 μM | | |
| PerSt73R (SEQ ID NO: 12) | 12 pMole | 0.4 μM | | |
| SIS1T74F (SEQ ID NO: 6) | 12 pMole | 0.4 μM | | |
| SIS1T75R (SEQ ID NO: 5) | 12 pMole | 0.4 μM | | |
| Probes | | | 5' Fluor | Quencher |
| Perstalt166p (SEQ ID NO: 24) | 5 pMole | 0.17 μM | FAM | BHQ1 |
| SIS1T65P (SEQ ID NO: 25) | 10 pMole | 0.33 μM | Quasar 670 | BHQ2 |
| wbdRa1P (SEQ ID NO: 26) | 12.5 pMole | 0.42 μM | CalFlour Orange | BHQ1 |

For Table 8, the thermal cycling conditions were: 2 minutes at 94° C., followed by 40 cycles of 94° C. for 15 seconds and 60° C. for 60 seconds, with the fluorescent signal captured during the 60° C. step at each cycle.

TABLE 12

| Primers | Per 30 μl reaction | Concentration in Reaction | 5' Fluor | Quencher |
|---|---|---|---|---|
| wbdra2R (SEQ ID NO: 16) | 20 pMole | 0.5 μM | | |
| PerSt73R (SEQ ID NO: 12) | 20 pMole | 0.4 μM | | |
| SIS1T75R (SEQ ID NO: 5) | 12 pMole | 0.4 μM | | |
| Unimolecular Scorpion | | | 5' Fluor | Quencher |
| SV40 scorpion 1 (SEQ ID NO: 29) | 10 pMole | 0.33 μM | TAMRA | BHQ2 |
| SIS1 scorpion 1 (SEQ ID NO: 4) | 10 pMole | 0.33 μM | Quasar670 | BHQ2 |
| WBDR scorpion 1 (SEQ ID NO: 15) | 15 pMole | 0.5 μM | CalFlour Orange | BHQ1 |

TABLE 12-continued

| Bimolecular Scorpion | | | | | |
|---|---|---|---|---|---|
| PERSYNA probe 1 (SEQ ID NO: 10 | 20 pMole | 0.66 μM | — | BHQ1 |
| PERSYNA probe 1 (SEQ ID NO: 11 | 5 pMole | 0.17 μM | 6FAM | — |

For Table 9, the thermal cycling conditions were: 2 minutes at 94° C., followed by 40 cycles of 94° C. for 15 seconds and 60° C. for 40 seconds, with the fluorescent signal captured during the 60° C. step at each cycle.

At 24 hours of incubation all enrichments that had tested negative by either the USDAMLG method or the method of the present invention were removed from the incubator and sampled for culture confirmation using the procedure as described in the USDA MLG.

Results:

Each sample is identified by run (A, B or C) followed by sample number for that run. For each run, numbers 1-25 represent samples that received an inoculum while number 26 is the media control blank. The targeted spike level for each run was 1.5 CFU/375 g beef sample. At this level not all samples would be expected to have actually received an inoculum cell due to poisson distribution. This is confirmed in Table 13, below, which gives the number of colonies on replicate plates each inoculated with 1× the inoculum used to spike the beef on that day and the number of enrichments that were positive in the run.

TABLE 13

| Run | Plate 1 (1X inoculum) | Plate 1 (1X inoculum) | Plate 1 (1X inoculum) | Average | Number positive of 25 spiked samples |
|---|---|---|---|---|---|
| A | 1 | 2 | 2 | 1.67 | 22 |
| B | 2 | 0 | 2 | 1.33 | 20 |
| C | 1 | 3 | 2 | 2.0 | 22 |

This data was used to generate a Most Probable Number (MPN) calculation in CFU/375 g sample for each run with 95% confidence intervals, as shown in Table 14 below.

TABLE 14

| Run | Number positive of 25 | Calculated MPN | 95% CI |
|---|---|---|---|
| A | 22 | 2.1 | 1.3-3.5 |
| B | 20 | 1.6 | 0.99-2.6 |
| C | 22 | 2.1 | 1.3-3.5 |

The results of all of this testing is given in Table 15, below.

TABLE 15

| Sample | USDAMLG standard method | Present Invention Method | Culture confirmation |
|---|---|---|---|
| A1 | POSITIVE | POSITIVE | ND |
| A2 | NEGATIVE | NEGATIVE | ND |
| A3 | POSITIVE | POSITIVE | ND |
| A4 | POSITIVE | POSITIVE | ND |
| A5 | POSITIVE | POSITIVE | ND |
| A6 | NEGATIVE | NEGATIVE | NEGATIVE |
| A7 | POSITIVE | POSITIVE | ND |
| A8 | POSITIVE | POSITIVE | ND |
| A9 | POSITIVE | POSITIVE | ND |
| A10 | POSITIVE | POSITIVE | ND |
| A11 | POSITIVE | POSITIVE | ND |
| A12 | POSITIVE | POSITIVE | ND |
| A13 | POSITIVE | POSITIVE | ND |
| A14 | POSITIVE | POSITIVE | ND |
| A15 | NEGATIVE | NEGATIVE | NEGATIVE |
| A16 | POSITIVE | POSITIVE | ND |
| A17 | POSITIVE | POSITIVE | ND |
| A18 | POSITIVE | POSITIVE | ND |
| A19 | POSITIVE | POSITIVE | ND |
| A20 | POSITIVE | POSITIVE | ND |
| A21 | POSITIVE | POSITIVE | ND |
| A22 | POSITIVE | POSITIVE | ND |
| A23 | POSITIVE | POSITIVE | ND |
| A24 | POSITIVE | POSITIVE | ND |
| A25 | POSITIVE | POSITIVE | ND |
| A26 | NEGATIVE | NEGATIVE | NEGATIVE |
| B1 | NEGATIVE | NEGATIVE | NEGATIVE |
| B2 | NEGATIVE | NEGATIVE | NEGATIVE |
| B3 | POSITIVE | POSITIVE* | ND |
| B4 | POSITIVE | POSITIVE | ND |
| B5 | POSITIVE | POSITIVE | ND |
| B6 | POSITIVE | POSITIVE | ND |
| B7 | POSITIVE | POSITIVE | ND |
| B8 | POSITIVE | POSITIVE | ND |
| B9 | POSITIVE | POSITIVE | ND |
| B10 | POSITIVE | POSITIVE | ND |
| B11 | POSITIVE | POSITIVE | ND |
| B12 | POSITIVE | POSITIVE | ND |
| B13 | POSITIVE | POSITIVE | ND |
| B14 | POSITIVE | POSITIVE | ND |
| B15 | POSITIVE | POSITIVE | ND |
| B16 | POSITIVE | POSITIVE | ND |
| B17 | POSITIVE | POSITIVE | ND |
| B18 | POSITIVE | POSITIVE | ND |
| B19 | POSITIVE | POSITIVE | ND |
| B20 | NEGATIVE | NEGATIVE* | NEGATIVE |
| B21 | POSITIVE | POSITIVE | ND |
| B22 | NEGATIVE | NEGATIVE | NEGATIVE |
| B23 | POSITIVE | POSITIVE | ND |
| B24 | POSITIVE | POSITIVE | ND |
| B25 | NEGATIVE | NEGATIVE | NEGATIVE |
| B26 | NEGATIVE | NEGATIVE | NEGATIVE |
| C1 | POSITIVE | Indeterminate* | ND |
| C2 | POSITIVE | POSITIVE | ND |
| C3 | POSITIVE | POSITIVE | ND |
| C4 | POSITIVE | POSITIVE | ND |
| C5 | POSITIVE | POSITIVE | ND |
| C6 | POSITIVE | POSITIVE | ND |
| C7 | POSITIVE | POSITIVE | ND |
| C8 | POSITIVE | POSITIVE | ND |
| C9 | NEGATIVE | NEGATIVE | NEGATIVE |
| C10 | POSITIVE | POSITIVE | ND |
| C11 | POSITIVE | POSITIVE | ND |
| C12 | POSITIVE | POSITIVE | ND |
| C13 | POSITIVE | POSITIVE | ND |
| C14 | POSITIVE | POSITIVE | ND |
| C15 | POSITIVE | POSITIVE | ND |
| C16 | NEGATIVE | NEGATIVE | NEGATIVE |
| C17 | POSITIVE | POSITIVE | ND |
| C18 | POSITIVE | POSITIVE | ND |
| C19 | POSITIVE | POSITIVE | ND |
| C20 | POSITIVE | POSITIVE | ND |
| C21 | POSITIVE | POSITIVE* | ND |
| C22 | POSITIVE | POSITIVE | ND |
| C23 | POSITIVE | POSITIVE | ND |
| C24 | NEGATIVE | NEGATIVE | ND |

TABLE 15-continued

| Sample | USDAMLG standard method | Present Invention Method | Culture confirmation |
|---|---|---|---|
| C25 | POSITIVE | POSITIVE | ND |
| C26 | NEGATIVE | NEGATIVE | ND |

For the method of the present invention, a "Positive" sample was one in which all three markers used generated a positive result as called by the instrument. "Indeterminate" results were those in which two of the three markers generated a positive call by the instrument. One or no targets generating a positive call were Negative. * Indicates an initially indeterminate call which was retested, with the result of the retest reported. One sample, C1, was indeterminate initially and upon retest. This was the only discrepancy with the USDAMLG method.

Conclusion: The method of the present invention is able to reliably detect even a single E. coli O157:H7 contaminant in a 375 g beef trim sample.

Example 5

Comparative Sensitivity of Present Detection Methods Vs. USDA Standard Method in Produce Samples This study was performed to validate the ability of the present O157:H7 detection test and methods to consistently detect 1-3 CFU of E. coli O157:H7 in a lettuce or spinach sample.

Sample Preparation

E. coli O157:H7 strains were grown overnight in BHI broth inoculated with a single colony. For the spinach sample trial, the strain employed was DD1450, an E. coli O157:H7 strain within the DuPont Qualicon culture collection that was isolated from a human clinical sample. For the lettuce trial, the strain employed was DD12835, an E. coli O157:H7 strain obtained from the Pennsylvania State University Department of Veterinary Science E. coli Reference Center.

Samples of sufficient quantity to perform all testing and Most Probable Number (MPN) analysis were inoculated with target diluted in sterile 0.1% peptone water. Spike levels were set at levels likely to give fractional positive results (generally 1-3 cfu per analytical portion) and confirmed by plating from appropriate dilutions of the overnight BHI culture and MPN analysis on the day sample enrichment began.

Prior to inoculation, a sufficient portion was removed to perform all necessary negative controls. Since the naturally occurring incidence of E. coli O157:H7 is now so low in all matrices tested, no pre-screening of matrix was conducted. The ten unspiked control samples were for each replicate (five test and five reference method samples) to demonstrate no naturally present target. None of these unspiked samples tested positive.

Lettuce and spinach were purchased from local grocery stores. The produce was aseptically divided into portions for inoculation with the challenge organism and an additional portion for a negative control. Forty 25 g test portions were surface inoculated at ~1-3 cfu/25 g as well as additional material to be tested by MPN and were recombined to form a master sample which was mixed well. Analytical units of 25 g were removed from this master sample and placed into stomacher bags. After inoculation, samples were stored at 4° C. for 2-3 days to adapt the organism to the produce. An additional portion of inoculated sample was used to determine the inoculation level using Most Probable Number (MPN) analysis (3×100 g, 3×10 g and 3×1 g). Ten 25 g portions of uninoculated produce were prepared as negative controls.

Comparative Method:

For the comparative test (FDA-BAM), produce samples (25 g) were diluted 1:10 with EEB. Contents were mixed by stomaching briefly (10-30 sec) and allowed to incubate at 37±0.5° C. with shaking for 24±2 hr. Enriched samples were spread in 10-uL aliquot of undiluted enrichment onto TCSMAC plate and in 0.1 mL aliquot of a 1:10 dilution onto another TCSMAC plate for isolation. All TCSMAC plates were incubated for 18-24 hr at 35-37° C., after which plates were examined for colonies with typical characteristics of E. coli O157:H7. Suspect colonies (up to five per plate when present) were confirmed using the biochemical and serological methods described in the FDA-BAM.

Test Method

For the method of the present invention, produce samples (25 g) were diluted with 225 mL pre-warmed BAX® System E. coli O157:H7 MP broth and incubated for 24 hr at 42° C.±2° C., sampling at 8, 10, and 24 hours with BAX® System assay. All samples, without respect to presumptive result, were subjected to culture confirmation as in the reference method.

Cultures were struck for purity on BHI agar. For each strain, one colony was inoculated into a tube containing BHI broth (exclusivity testing) or test broth enrichment (inclusivity testing). Cultures were incubated overnight at 35° C. to reach cell densities of approximately $10^9$ bacterial cells per mL. For exclusivity testing, cultures were tested with no dilution. For inclusivity testing, cultures were diluted to $10^5$ cfu/mL, which is ~1 log over the claimed sensitivity of the assay. 20 µl of the material to be tested was added to 200 µl of BAX® lysis reagent (DuPont Qualicon, Wilmington, Del.). The mixture was incubated at 37° C. for 20 minutes, then further incubated at 95° C. for 10 minutes, and finally cooled to 5° C.

30 µl of the DNA lysate as prepared above was used to hydrate lyophilized PCR reaction components to achieve a DNA lysate/PCR reaction component mixture containing the primers and probes listed in Table 16.

TABLE 16

| Primers | Per reaction |
|---|---|
| wbdra2R (SEQ ID NO: 16) | 20 pMole |
| SIS1T75R (SEQ ID NO: 5) | 20 pMole |
| SV40-33-4312 (SEQ ID NO: 27) | 20 pMole |
| SV40-29-4222 (SEQ ID NO: 28) | 2.5 pMole |

TABLE 16-continued

| Probes | Per reaction | 5' Fluor | Quencher |
|---|---|---|---|
| WBDR scorpion 1 (SEQ ID NO: 15) | 15 pMole | Calflour Orange 560 | BHQ1 |
| SIS1 scorpion 1 (SEQ ID NO: 4) | 5 pMole | Quasar 670 | BHQ2 |
| SV40 scorpion 1 (SEQ ID NO: 29) | 5 pMole | TAMRA | BHQ2 |

SEQ ID NO:15 (WBDR scorpion 1 probe) is presented in the sequence listing as the entire sequence without modifications. For this Example, the WBDR scorpion probe has, following nucleotide number 45 in SEQ ID NO:15, an internal BHQ1 quencher and an SP-18 blocker followed by the remaining 42 nucleotides. Similarly, SEQ ID NO:4 (SIS1 scorpion 1 probe) is presented in the sequence listing as the entire sequence without modifications. For this Example, the SIS1 scorpion probe has, following nucleotide number 46 in SEQ ID NO:4, an internal BHQ2 quencher and an SP-18 blocker followed by the remaining 40 nucleotides. Also, SEQ ID NO:29 (SV40 scorpion 1 probe) is presented in the sequence listing as the entire sequence without modifications. For this Example, the SV40 scorpion probe has, following nucleotide number 52 in SEQ ID NO:29, an internal BHQ2 quencher and an SP-18 blocker followed by the remaining 26 nucleotides.

The DNA lysate/PCR reaction component mixture was added to a PCR reaction mixture comprising typical PCR ingredients including nucleotides, Taq polymerase and reaction buffer to perform PCR.

Amplification and testing was performed on the BAX® Q7 machine (DuPont Qualicon, Wilmington, Del.). The thermal cycling conditions were: 2 minutes at 94° C., followed by 40 cycles of 94° C. for 10 seconds and 63° C. for 40 seconds, with the fluorescent signal captured during the 63° C. step at each cycle.

At 24 hours of incubation, all enrichments that had tested negative by either the USDA MLG method or the method of the present invention were removed from the incubator and sampled for culture confirmation using the procedure as described in the USDA MLG.

Data Analysis:

Data analysis was performed according to the AOAC guidelines for microbiological method validation. Most probable number (MPN) of colony forming units per test portion was performed on the day of testing using the reference method. MPN values were calculated using the tables found in the FDA-BAM. Spike level was determined by performing a standard plate count on the incident cultures which were diluted for spiking each matrix on the day of introduction to the master sample. Sensitivity rate is calculated as 100 times the number of true presumptive positive results divided by total true positive results confirmed from enrichment of spiked samples. False negative rate was calculated as 100 minus sensitivity rate. Specificity rate was calculated as 100 times the number of assay-negative results divided by total number of true negative results, including unspiked samples. False positive rate was calculated as 100 minus specificity rate. A Chi square test for significant difference was performed using the McNemar formula: $(|a-b|-1)^2/(a+b)$, where a=results that were positive by BAX and negative by reference method, and b=results that were negative by BAX and positive by reference method used for paired samples, Mantel Haenszel for unpaired samples. A Chi square value of less than 3.84 indicates no significant difference, at the 95% confidence level, between the two methods, while a Chi square value of greater than 3.84 indicates a significant difference between the test and reference methods.

Results and Conclusion

As shown in Tables 17 and 18, below, using produce enrichments (lettuce and spinach) as samples, the test method demonstrated equivalent or superior performance relative to the reference method.

TABLE 17

Results of 25 g Lettuce Spiked with Strain DD12835

| Method | MPN Per 25 g | Spike Level | Enrichment Method (Media) | Total spiked | Presump Pos/Confirmed | Sensitivity % | False Neg % | Presump. Pos/Unspiked | Specificity % | False Pos % | Chi-square |
|---|---|---|---|---|---|---|---|---|---|---|---|
| 8 hr BAX | 1.1 | 1.0 | BAX MP | 20 | 15/16 | 94 | 6 | 0/5 | 100 | 0 | 6.3 |
| 10 hr BAX | 1.1 | 1.0 | BAX MP | 20 | 15/16 | 94 | 6 | 0/5 | 100 | 0 | 6.3 |
| 24 hr BAX | 1.1 | 1.0 | BAX MP | 20 | 16/16 | 100 | 0 | 0/5 | 100 | 0 | 8.1 |
| Reference (24 hr) | 1.1 | 1.0 | EEB | 20 | 7 | NA | NA | 0/5 | NA | NA | |

TABLE 18

Results of 25 g Spinach Spiked with Strain DD1450

| Method | MPN Per 25 g | Spike Level | Enrichment Method (Media) | Total spiked | Presump Pos/Confirmed | Sensitivity % | False Neg % | Presump. Pos/Unspiked | Specificity % | False Pos % | Chi-square |
|---|---|---|---|---|---|---|---|---|---|---|---|
| 8 hr BAX | 0.23 | 1.0 | BAX MP | 20 | 12/13 | 92 | 8 | 0/5 | 100 | 0 | 3.6 |
| 10 hr BAX | 0.23 | 1.0 | BAX MP | 20 | 13/13 | 100 | 0 | 0/5 | 100 | 0 | 4.8 |
| 24 hr BAX | 0.23 | 1.0 | BAX MP | 20 | 13/13 | 100 | 0 | 0/5 | 100 | 0 | 4.8 |

TABLE 18-continued

Results of 25 g Spinach Spiked with Strain DD1450

| Method | MPN Per 25 g | Spike Level | Enrichment Method (Media) | Total spiked | Presump Pos/Confirmed | Sensitivity % | False Neg % | Presump. Pos/Unspiked | Specificity % | False Pos % | Chi-square |
|---|---|---|---|---|---|---|---|---|---|---|---|
| Reference (24 hr) | 0.23 | 1.0 | EEB | 20 | 6 | NA | NA | 0/5 | NA | NA | |

What is claimed is:

1. A method for detecting the presence of *E. coli* O157:H7 in a sample, said sample comprising nucleic acids, said method comprising:
   (a) providing a reaction mixture comprising suitable primer pairs for amplification of at least portions of
   (i) two or more regions of pO157 of the *E. coli* O157:H7 genome, wherein said primer pairs are suitable for amplification of SEQ ID NO: 2 and SEQ ID NO: 3, wherein said primer pair for amplification of the nucleic acid region of SEQ ID NO: 2 comprises SEQ ID NO: 12 and SEQ ID NO: 13, wherein said primer pair for amplification of the nucleic acid region of SEQ ID NO: 3 comprises SEQ ID NO:16 and SEQ ID NO:17, and
   (ii) one or more *E. coli* O157:H7 genomic DNA regions outside the pO157 portion of the *E. coli* O157:H7 genome, wherein said primer pair is suitable for amplification of SEQ ID NO: 1, and wherein said primer pair for amplification of SEQ ID NO: 1 comprises SEQ ID NO:5 and SEQ ID NO:6;

(b) performing PCR amplification of said nucleic acids of said sample using the reaction mixture of step (a); and
(c) detecting the amplification of step (b), whereby a positive detection of amplification in (a)(i) and (a)(ii) indicates the presence of *E. coli* O157:H7 in the sample.

2. The method of claim 1, wherein said reaction mixture further comprises one nucleic acid probe for each nucleic acid region selected.

3. The method of claim 2, wherein said nucleic acid probes comprise one or more of SEQ ID NO:7, SEQ ID NO:14, and SEQ ID NO:18.

4. The method of claim 1, wherein the sample comprises a food sample or a water sample.

\* \* \* \* \*